United States Patent
Kim et al.

(10) Patent No.: US 11,058,884 B2
(45) Date of Patent: Jul. 13, 2021

(54) WEARABLE MEDICAL (WM) SYSTEM MONITORING ECG SIGNAL OF AMBULATORY PATIENT FOR HEART CONDITION

(71) Applicant: West Affum Holdings Corp., Grand Cayman (KY)

(72) Inventors: Jaeho Kim, Redmond, WA (US); Pamela Breske, Newcastle, WA (US); Gregory T. Kavounas, Bellevue, WA (US)

(73) Assignee: West Affum Holding Corp, Grand Cayman (KY)

( * ) Notice: Subject to any disclaimer, the term of this patent is extended or adjusted under 35 U.S.C. 154(b) by 272 days.

(21) Appl. No.: 16/392,541

(22) Filed: Apr. 23, 2019

(65) Prior Publication Data
US 2019/0329052 A1 Oct. 31, 2019

Related U.S. Application Data

(60) Provisional application No. 62/662,905, filed on Apr. 26, 2018.

(51) Int. Cl.
*A61N 1/39* (2006.01)
*A61B 5/046* (2006.01)
(Continued)

(52) U.S. Cl.
CPC .............. *A61N 1/3904* (2017.08); *A61B 5/25* (2021.01); *A61B 5/316* (2021.01); *A61B 5/349* (2021.01);
(Continued)

(58) Field of Classification Search
CPC .... A61N 1/3904; A61N 1/3987; A61B 5/361; A61B 5/349; A61B 5/316; A61B 5/25;
(Continued)

(56) References Cited

U.S. PATENT DOCUMENTS 3,724,355 A 4/1973 Unger
4,583,524 A 4/1986 Hutchins et al.
(Continued)

FOREIGN PATENT DOCUMENTS

EP 0835635 A1 4/1998
WO 98/39061 A2 9/1998

OTHER PUBLICATIONS

Pagan-Carlo, et al., "Encircling Overlapping Multipulse Shock Waveforms for Transthoracic Defibrillation," JACC Journals, Dec. 1998, vol. 32 Issue 7, p. 2065-2071.
(Continued)

*Primary Examiner* — Erin M Piateski
(74) *Attorney, Agent, or Firm* — Spectrum IP Law Group LLC

(57) ABSTRACT

In embodiments, a wearable medical (WM) system includes ECG electrodes, and a support structure that can be worn by an ambulatory patient so as to maintain the ECG electrodes on the patient's body. When thus maintained, the ECG electrodes can be configured to sense an ECG signal of the ambulatory patient. The WM system further includes a memory that stores a reference template, and an output device. The reference template can be made from one or more early portions of the ECG signal of the patient. Then later portions of the ECG signal are sensed and compared against the reference template, to determine if there is a specific problem. If it is so determined, the output device can output an alert.

38 Claims, 23 Drawing Sheets

(51) Int. Cl.
*A61B 5/0408* (2006.01)
*A61B 5/04* (2006.01)
*A61B 5/25* (2021.01)
*A61B 5/316* (2021.01)
*A61B 5/349* (2021.01)
*A61B 5/361* (2021.01)
*A61B 5/00* (2006.01)
*A61B 5/352* (2021.01)
*A61B 5/363* (2021.01)
*A61B 5/364* (2021.01)
*A61B 5/366* (2021.01)

(52) U.S. Cl.
CPC ............ *A61B 5/361* (2021.01); *A61N 1/3987* (2013.01); *A61B 5/352* (2021.01); *A61B 5/363* (2021.01); *A61B 5/364* (2021.01); *A61B 5/366* (2021.01); *A61B 5/6805* (2013.01); *A61B 5/6823* (2013.01); *A61B 5/6831* (2013.01)

(58) Field of Classification Search
CPC ......... A61B 5/364; A61B 5/363; A61B 5/352; A61B 5/366; A61B 5/6805; A61B 5/6823; A61B 5/6831
USPC ........................................................ 600/509
See application file for complete search history.

(56) References Cited

U.S. PATENT DOCUMENTS

| | | | |
|---|---|---|---|
| 4,619,265 A | 10/1986 | Morgan et al. | |
| 4,928,690 A | 5/1990 | Heilman et al. | |
| 4,955,381 A | 9/1990 | Way et al. | |
| 5,078,134 A | 1/1992 | Heilman et al. | |
| 5,228,449 A | 7/1993 | Christ et al. | |
| 5,348,008 A | 9/1994 | Bomn et al. | |
| 5,353,793 A | 10/1994 | Bomn | |
| RE34,800 E | 11/1994 | Hutchins | |
| 5,394,892 A | 3/1995 | Kenny | |
| 5,405,362 A | 4/1995 | Kramer et al. | |
| 5,474,574 A | 12/1995 | Payne et al. | |
| 5,662,690 A | 9/1997 | Cole et al. | |
| 5,782,878 A | 7/1998 | Morgan et al. | |
| 5,792,204 A | 8/1998 | Snell | |
| 5,902,249 A | 5/1999 | Lyster | |
| 5,913,685 A | 6/1999 | Hutchins | |
| 5,944,669 A | 8/1999 | Kaib | |
| 6,047,203 A | 4/2000 | Sackner et al. | |
| 6,065,154 A | 5/2000 | Hulings et al. | |
| 6,108,197 A | 8/2000 | Janik | |
| 6,148,233 A | 11/2000 | Owen et al. | |
| 6,201,992 B1 | 3/2001 | Freeman | |
| 6,263,238 B1 | 7/2001 | Brewer et al. | |
| 6,287,328 B1 | 9/2001 | Snyder et al. | |
| 6,304,780 B1 | 10/2001 | Owen et al. | |
| 6,319,011 B1 | 11/2001 | Moth et al. | |
| 6,334,070 B1 | 12/2001 | Nova et al. | |
| 6,356,785 B1 | 3/2002 | Snyder | |
| 6,427,083 B1 | 7/2002 | Owen et al. | |
| 6,437,083 B1 | 7/2002 | Owen et al. | |
| 6,529,875 B1 | 3/2003 | Nakajima | |
| 6,546,285 B1 | 4/2003 | Owen et al. | |
| 6,671,545 B2 | 12/2003 | Fincke | |
| 6,681,003 B2 | 1/2004 | Linder et al. | |
| 6,762,917 B1 | 7/2004 | Verbiest et al. | |
| 7,065,401 B2 | 6/2006 | Worden | |
| 7,559,902 B2 | 7/2009 | Ting et al. | |
| 7,865,238 B2 | 1/2011 | Brink | |
| 7,870,761 B2 | 1/2011 | Valentine et al. | |
| 7,974,689 B2 | 7/2011 | Volpe et al. | |
| 8,135,462 B2 | 3/2012 | Owen et al. | |
| 8,140,154 B2 | 3/2012 | Donnelly et al. | |
| 8,369,944 B2 | 2/2013 | Macho et al. | |
| 8,548,557 B2 | 10/2013 | Garstka et al. | |
| 8,615,295 B2 | 12/2013 | Savage et al. | |
| 8,644,925 B2 | 2/2014 | Volpe et al. | |
| 8,897,860 B2 | 11/2014 | Volpe et al. | |
| 8,904,214 B2 | 12/2014 | Volpe et al. | |
| 8,965,500 B2 | 2/2015 | Macho et al. | |
| 9,008,801 B2 | 4/2015 | Kaib et al. | |
| 9,089,685 B2 | 7/2015 | Sullivan et al. | |
| 9,131,901 B2 | 9/2015 | Volpe et al. | |
| 9,132,267 B2 | 9/2015 | Kaib | |
| 9,408,548 B2 | 8/2016 | Volpe et al. | |
| 9,454,219 B2 | 9/2016 | Volpe et al. | |
| 9,592,403 B2 | 3/2017 | Sullivan | |
| 2003/0158593 A1 | 8/2003 | Heilman et al. | |
| 2004/0059237 A1 | 3/2004 | Narayan et al. | |
| 2005/0107833 A1 | 5/2005 | Freeman et al. | |
| 2005/0107834 A1 | 5/2005 | Freeman et al. | |
| 2005/0149125 A1* | 7/2005 | Kim ...................... A61B 5/363 607/5 |
| 2008/0312709 A1 | 12/2008 | Volpe et al. | |
| 2009/0005827 A1 | 1/2009 | Weintraub et al. | |
| 2010/0007413 A1 | 1/2010 | Herleikson | |
| 2010/0298899 A1 | 11/2010 | Donnelly et al. | |
| 2011/0022105 A9 | 1/2011 | Owen et al. | |
| 2011/0288604 A1 | 11/2011 | Kaib et al. | |
| 2011/0288605 A1 | 11/2011 | Kaib et al. | |
| 2012/0112903 A1 | 5/2012 | Kaib et al. | |
| 2012/0144551 A1 | 6/2012 | Guldalian | |
| 2012/0150008 A1 | 6/2012 | Kaib et al. | |
| 2012/0158075 A1 | 6/2012 | Kaib et al. | |
| 2012/0265265 A1 | 10/2012 | Razavi et al. | |
| 2012/0283794 A1 | 11/2012 | Kaib et al. | |
| 2012/0293323 A1 | 11/2012 | Kaib et al. | |
| 2012/0302860 A1 | 11/2012 | Volpe et al. | |
| 2012/0310315 A1 | 12/2012 | Savage et al. | |
| 2013/0085538 A1 | 4/2013 | Volpe et al. | |
| 2013/0231711 A1 | 9/2013 | Kaib et al. | |
| 2013/0245388 A1 | 9/2013 | Rafferty et al. | |
| 2013/0274565 A1 | 10/2013 | Langer et al. | |
| 2013/0317852 A1 | 11/2013 | Worrell et al. | |
| 2013/0325078 A1 | 12/2013 | Whiting et al. | |
| 2014/0025131 A1 | 1/2014 | Sullivan et al. | |
| 2014/0070957 A1 | 3/2014 | Longinotti-Buitoni et al. | |
| 2014/0163663 A1 | 6/2014 | Poddar et al. | |
| 2014/0324112 A1 | 10/2014 | Macho et al. | |
| 2014/0364918 A1 | 12/2014 | Owen et al. | |
| 2014/0378812 A1 | 12/2014 | Saroka et al. | |
| 2015/0039053 A1 | 2/2015 | Kaib et al. | |
| 2015/0297904 A1* | 10/2015 | Kavounas ............ A61B 5/6843 607/6 |
| 2015/0328472 A1 | 11/2015 | Sullivan et al. | |
| 2016/0004831 A1 | 1/2016 | Carlson et al. | |
| 2016/0082277 A1 | 3/2016 | Foshee, Jr. et al. | |
| 2018/0350468 A1* | 12/2018 | Friedman ............... A61B 5/349 |
| 2019/0282823 A1* | 9/2019 | Freeman ............... A61N 1/3943 |

OTHER PUBLICATIONS

Klein, H. U., Goldenberg I., & Moss, A. J., Risk Stratification for Implantable Cardioverter Defibrillator Therapy: The Role of the Wearable Cardioverter-Defibrillator, Clinical update, European Heart Journal, May 31, 2013, pp. 1-14, doi:10.1093/eurheartj/eht167, European Society of Cardiology.
LIFECOR LifeVest System Model WCD 3100 Operator's Manual, 2006, PN 20B0040 Rev FI, Zoll Lifecor Corporation, Pittsburgh, PA.
LifeVest Model 4000 Patient Manual, Zoll, 2009, PN 20B0047 Rev B.
Heartstart MRx and XL AED Algorithm—Application Note, Jul. 2001, Edition 2 Philips Healthcare, USA.
The LifeVest Network/Patient Data Management System, Zoll, 2015, 20C0503 Rev A.
EP Examination Search and Examination report dated Dec. 4, 2019, to EP Patent Application No. 19171211.6.

* cited by examiner

SAMPLE COMPONENTS OF WEARABLE CARDIOVERTER DEFIBRILLATOR (WCD) SYSTEM

SAMPLE COMPONENTS OF EXTERNAL DEFIBRILLATOR

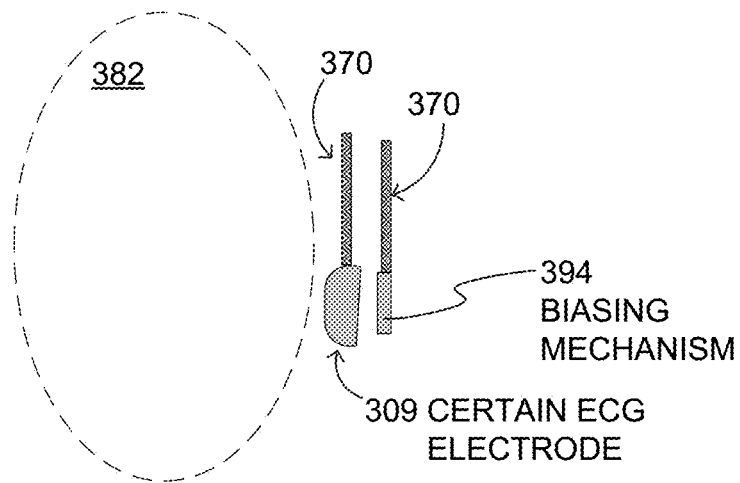
FIG. 3A *ELECTRODE UNBIASED TOWARDS BODY*
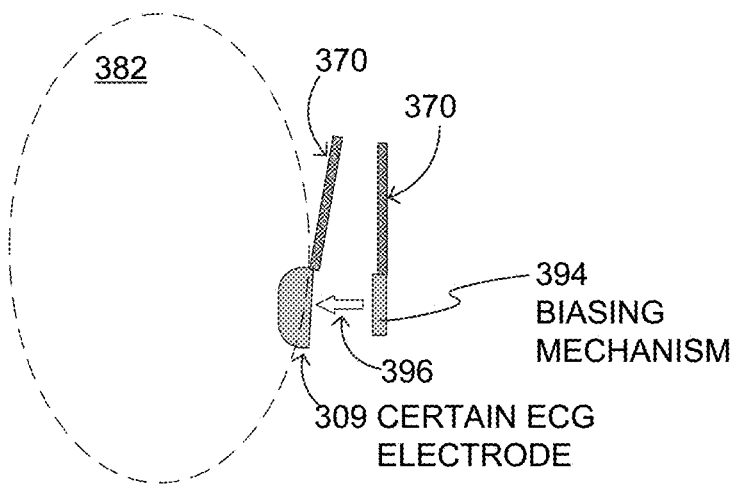
FIG. 3B *ELECTRODE BIASED TOWARDS BODY*

COMPONENTS OF
SAMPLE WCD SYSTEM

*MULTIPLE ELECTRODES FOR SENSING ECG SIGNALS ALONG DIFFERENT VECTORS*

*COMPONENTS OF SAMPLE WM SYSTEM*

SAMPLE MONITORED ASPECTS
OF ECG SIGNAL

FIG. 11    METHODS $$FCC = \frac{\left(N \sum_{i=1}^{N} x_i y_i - \left(\sum_{i=1}^{N} x_i\right)\left(\sum_{i=1}^{N} y_i\right)\right)^2}{\left(N \sum_{i=1}^{N} x_i^2 - \left(\sum_{i=1}^{N} x_i\right)^2\right)\left(N \sum_{i=1}^{N} y_i^2 - \left(\sum_{i=1}^{N} y_i\right)^2\right)}$$

*BREATHING SENSOR*

*COMPONENT OF PATIENT SWEAT SENSOR*

*SWEAT SENSOR*

*WEARABLE MEDICAL SYSTEM PACING TO CORRECT HEART FAILURE*

*WEARABLE MEDICAL SYSTEM PACING TO CORRECT HEART FAILURE*

WEARABLE MEDICAL (WM) SYSTEM MONITORING ECG SIGNAL OF AMBULATORY PATIENT FOR HEART CONDITION

CROSS REFERENCE TO RELATED PATENT APPLICATIONS

This patent application claims priority from U.S. provisional patent application Ser. No. 62/662,905, filed on Apr. 26, 2018.

BACKGROUND

When people suffer from some types of heart arrhythmias, the result may be that blood flow to various parts of the body is reduced. Some arrhythmias may even result in a Sudden Cardiac Arrest (SCA). SCA can lead to death very quickly, e.g. within 10 minutes, unless treated in the interim. Some observers have thought that SCA is the same as a heart attack, which it is not.

Some people have an increased risk of SCA. Such people include patients who have had a heart attack, or a prior SCA episode. A frequent recommendation for these people is to receive an Implantable Cardioverter Defibrillator (ICD). The ICD is surgically implanted in the chest, and continuously monitors the patient's electrocardiogram (ECG). If certain types of heart arrhythmias are detected, then the ICD delivers an electric shock through the heart.

People who have been identified to have an increased risk of an SCA are sometimes given a Wearable Cardioverter Defibrillator (WCD) system, to wear until the time that their ICD is implanted. Early versions of such systems were called wearable cardiac defibrillator systems. A WCD system typically includes a harness, vest, belt, or other garment that the patient is to wear. The WCD system further includes electronic components, such as a defibrillator and electrodes, coupled to the harness, vest, or other garment. When the patient wears the WCD system, the electrodes may make good electrical contact with the patient's skin, and therefore can help sense the patient's ECG. If a shockable heart arrhythmia is detected from the ECG, then the defibrillator delivers an appropriate electric shock through the patient's body, and thus through the heart. This may restart the patient's heart and thus save their life.

All subject matter discussed in this Background section of this document is not necessarily prior art, and may not be presumed to be prior art simply because it is presented in this Background section. Plus, any reference to any prior art in this description is not, and should not be taken as, an acknowledgement or any form of suggestion that such prior art forms parts of the common general knowledge in any art in any country. Along these lines, any recognition of problems in the prior art discussed in this Background section or associated with such subject matter should not be treated as prior art, unless expressly stated to be prior art. Rather, the discussion of any subject matter in this Background section should be treated as part of the approach taken towards the particular problem by the inventors. This approach in and of itself may also be inventive.

BRIEF SUMMARY

The present description gives instances of wearable medical (WM) systems, devices, storage media that may store programs, and methods, the use of which may help overcome problems and limitations of the prior art.

In embodiments, a wearable medical (WM) system includes ECG electrodes, and a support structure that can be worn by an ambulatory patient so as to maintain the ECG electrodes on the patient's body. When thus maintained, the ECG electrodes can be configured to sense an ECG signal of the ambulatory patient. The WM system further includes a memory that stores a reference template, and an output device. The reference template can be made from one or more early portions of the ECG signal of the patient. Then later portions of the ECG signal are sensed and compared against the reference template, to determine if there is a specific problem. If it is so determined, the output device can output an alert.

In embodiments, a wearable medical (WM) system includes a support structure that can be worn by an ambulatory patient, and a monitoring device that monitors a physiological parameter of the patient other than an ECG signal of the patient. The WM system further includes a memory that stores one or more myocardial infarction (MI) alarm conditions that are related to a myocardial infarction, and an output device. A value of the monitored physiological parameter is input, and it is determined whether or not that value meets at least one of the one or more MI alarm conditions. If it is so determined, the output device can output an alert.

In embodiments, a sweat sensor may detect sweating by a person. The sensor includes a tube having a cavity and two openings. A support structure that the person wears maintains the tube on the person's body at one of the openings. Any sweating by the person is ventilated to the outside by the other of the openings. Sudden changes in humidity of the air within the cavity may signify sudden and profuse sweating of the patient. The sensor also includes a hygrometer within the cavity for sensing that humidity. The sensor may communicate the measured humidity, or its change, to a different module. The sensor may be made economically, and detection of sweating may prove useful in detecting that the person is having a myocardial infarction, also known as heart attack.

These and other features and advantages of the claimed invention will become more readily apparent in view of the embodiments described and illustrated in this specification, namely in this written specification and the associated drawings.

BRIEF DESCRIPTION OF THE DRAWINGS

FIG. 3A is a diagram showing an electrode, such as a possible embodiment of an electrode of FIG. 1, which is not being biased towards the body of the wearer according to embodiments.

FIG. 3B is a diagram showing the electrode of FIG. 3A, but in which the electrode is instead being biased towards the body of the wearer according to embodiments.

FIG. 13 shows a sample equation for computing a waveform similarity coefficient according to embodiments, for detecting suspect ECG waveforms such as some of the waveforms in FIG. 12.

DETAILED DESCRIPTION

As has been mentioned, the present description is about wearable medical (WM) systems, devices, storage media that may store programs, and methods. Embodiments are now described in more detail.

A wearable cardioverter defibrillator (WCD) system according to embodiments may protect an ambulatory patient by electrically restarting their heart if needed. Such a WCD system may have a number of components. These components can be provided separately as modules that can be interconnected, or can be combined with other components, and so on.

Figure 1:
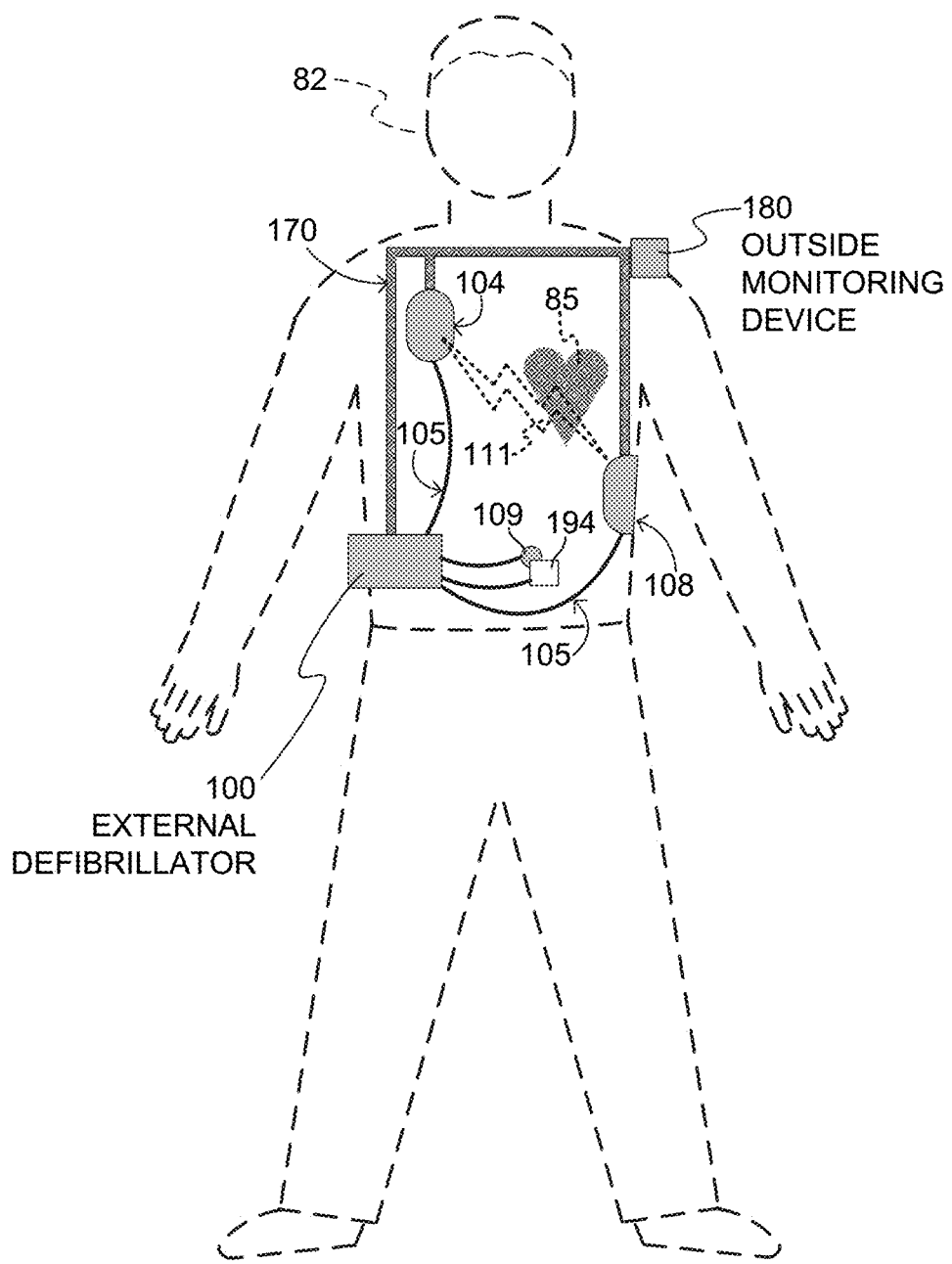
FIG. 1 is a diagram of components of a sample wearable cardioverter defibrillator (WCD) system, made according to embodiments.

FIG. 1 depicts a patient 82. Patient 82 may also be referred to as a person and/or wearer, since the patient is wearing components of the WCD system. Patient 82 is ambulatory, which means that, while wearing the wearable portion of the WCD system, patient 82 can walk around and is not necessarily bed-ridden. While patient 82 may be considered to be also a "user" of the WCD system, this is not a requirement. For instance, a user of the wearable cardioverter defibrillator (WCD) may also be a clinician such as a doctor, nurse, emergency medical technician (EMT) or other similarly tasked individual or group of individuals. In some cases, a user may even be a bystander. The particular context of these and other related terms within this description should be interpreted accordingly.

A WCD system according to embodiments can be configured to defibrillate the patient who is wearing the designated parts the WCD system. Defibrillating can be by the WCD system delivering an electrical charge to the patient's body in the form of an electric shock. The electric shock can be delivered in one or more pulses.

In particular, FIG. 1 also depicts components of a WCD system made according to embodiments. One such component is a support structure 170 that is wearable by ambulatory patient 82. Accordingly, support structure 170 is configured to be worn by ambulatory patient 82 for at least several hours per day, and for at least several days, even a few months. It will be understood that support structure 170 is shown only generically in FIG. 1, and in fact partly conceptually. FIG. 1 is provided merely to illustrate concepts about support structure 170, and is not to be construed as limiting how support structure 170 is implemented, or how it is worn.

Support structure 170 can be implemented in many different ways. For example, it can be implemented in a single component or a combination of multiple components. In embodiments, support structure 170 could include a vest, a half-vest, a garment, etc. In such embodiments such items can be worn similarly to analogous articles of clothing. In embodiments, support structure 170 could include a harness, one or more belts or straps, etc. In such embodiments, such items can be worn by the patient around the torso, hips, over the shoulder, etc. In embodiments, support structure 170 can include a container or housing, which can even be waterproof. In such embodiments, the support structure can be worn by being attached to the patient's body by adhesive material, for example as shown and described in U.S. Pat. No. 8,024,037. Support structure 170 can even be implemented as described for the support structure of U.S. Pat. App. No. U.S. 2017/0056682, which is incorporated herein by reference. Of course, in such embodiments, the person skilled in the art will recognize that additional components of the WCD system can be in the housing of a support structure instead of being attached externally to the support structure, for example as described in the U.S. 2017/0056682 document. There can be other examples.

FIG. 1 shows a sample external defibrillator 100. As described in more detail later in this document, some aspects of external defibrillator 100 include a housing and an energy storage module within the housing. As such, in the context of a WCD system, defibrillator 100 is sometimes called a main electronics module. The energy storage module can be configured to store an electrical charge. Other components can cause at least some of the stored electrical charge to be discharged via electrodes through the patient, so as to deliver one or more defibrillation shocks through the patient.

FIG. 1 also shows sample defibrillation electrodes 104, 108, which are coupled to external defibrillator 100 via electrode leads 105. Defibrillation electrodes 104, 108 can be configured to be worn by patient 82 in a number of ways. For instance, defibrillator 100 and defibrillation electrodes 104, 108 can be coupled to support structure 170, directly or indirectly. In other words, support structure 170 can be configured to be worn by ambulatory patient 82 so as to maintain at least one of electrodes 104, 108 on the body of ambulatory patient 82, while patient 82 is moving around, etc. The electrode can be thus maintained on the body by being attached to the skin of patient 82, simply pressed against the skin directly or through garments, etc. In some embodiments the electrode is not necessarily pressed against the skin, but becomes biased that way upon sensing a condition that could merit intervention by the WCD system. In addition, many of the components of defibrillator 100 can be considered coupled to support structure 170 directly, or indirectly via at least one of defibrillation electrodes 104, 108.

When defibrillation electrodes 104, 108 make good electrical contact with the body of patient 82, defibrillator 100 can administer, via electrodes 104, 108, a brief, strong electric pulse 111 through the body. Pulse 111 is also known as shock, defibrillation shock, therapy, electrotherapy, therapy shock, etc. Pulse 111 is intended to go through and restart heart 85, in an effort to save the life of patient 82. Pulse 111 can further include one or more pacing pulses of lesser magnitude to simply pace heart 85 if needed, and so on.

A prior art defibrillator typically decides whether to defibrillate or not based on an ECG signal of the patient. However, external defibrillator 100 may initiate defibrillation, or hold-off defibrillation, based on a variety of inputs, with the ECG signal merely being one of these inputs. In this example, ECG electrodes are provided, of which ECG electrode 109 is shown. In addition, in this example, a biasing mechanism 194 is provided for biasing ECG electrode 109. More about such biasing mechanisms is described later in this document.

A WCD system according to embodiments can obtain data from patient 82. For collecting such data, the WCD system may optionally include at least an outside monitoring device 180. Device 180 is called an "outside" device because it could be provided as a standalone device, for example not within the housing of defibrillator 100. Device 180 can be configured to sense or monitor at least one local parameter. A local parameter can be a parameter of patient 82, or a parameter of the WCD system, or a parameter of the environment, as will be described later in this document.

For some of these parameters, device 180 may include one or more sensors or transducers. Each one of such sensors can be configured to sense a parameter of patient 82, and to render an input responsive to the sensed parameter. In some embodiments the input is quantitative, such as values of a sensed parameter; in other embodiments the input is qualitative, such as informing whether or not a threshold is crossed, and so on. Sometimes these inputs about patient 82 are also called physiological inputs and patient inputs. In embodiments, a sensor can be construed more broadly, as encompassing many individual sensors.

Optionally, device 180 is physically coupled to support structure 170. In addition, device 180 may be communicatively coupled with other components that are coupled to support structure 170. Such communication can be implemented by a communication module, as will be deemed applicable by a person skilled in the art in view of this description.

In embodiments, one or more of the components of the shown WCD system may be customized for patient 82. This customization may include a number of aspects. For instance, support structure 170 can be fitted to the body of patient 82. For another instance, baseline physiological parameters of patient 82 can be measured, such as the heart rate of patient 82 while resting, while walking, motion detector outputs while walking, etc. The measured values of such baseline physiological parameters can be used to customize the WCD system, in order to make its diagnoses more accurate, since patients' bodies differ from one another. Of course, such parameter values can be stored in a memory of the WCD system, and so on. Moreover, a programming interface can be made according to embodiments, which receives such measured values of baseline physiological parameters. Such a programming interface may input automatically in the WCD system these, along with other data.

Figure 2:
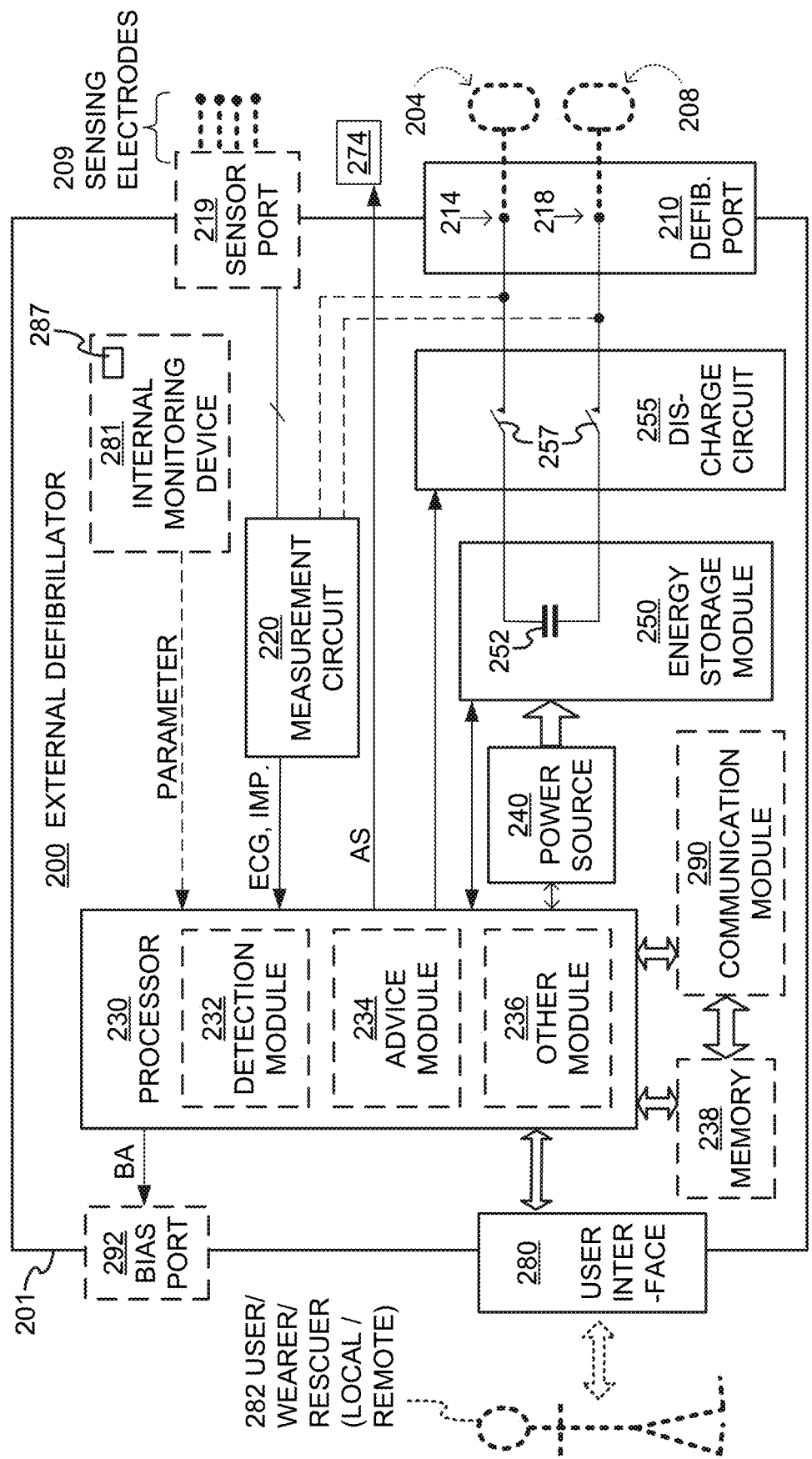
FIG. 2 is a diagram showing sample components of an external defibrillator, such as the one belonging in the system of FIG. 1, and which is made according to embodiments.

FIG. 2 is a diagram showing components of an external defibrillator 200, made according to embodiments. These components can be, for example, included in external defibrillator 100 of FIG. 1. The components shown in FIG. 2 can be provided in a housing 201, which may also be referred to as casing 201.

External defibrillator 200 is intended for a patient who would be wearing it, such as ambulatory patient 82 of FIG. 1. Defibrillator 200 may further include a user interface 280 for a user 282. User 282 can be patient 82, also known as wearer 82. Or, user 282 can be a local rescuer at the scene, such as a bystander who might offer assistance, or a trained person. Or, user 282 might be a remotely located trained caregiver in communication with the WCD system.

User interface 280 can be made in a number of ways. User interface 280 may include output devices, which can be visual, audible or tactile, for communicating to a user by outputting images, sounds or vibrations. Images, sounds, vibrations, and anything that can be perceived by user 282 can also be called human-perceptible indications (HPIs). There are many examples of output devices. For example, an output device can be a light, or a screen to display what is sensed, detected and/or measured, and provide visual feedback to rescuer 282 for their resuscitation attempts, and so on. Another output device can be a speaker, which can be configured to issue voice prompts, beeps, loud alarm sounds and/or words to warn bystanders, etc.

User interface 280 may further include input devices for receiving inputs from users. Such input devices may include various controls, such as pushbuttons, keyboards, touchscreens, one or more microphones, and so on. An input device can be a cancel switch, which is sometimes called an "I am alive" switch or "live man" switch. In some embodiments, actuating the cancel switch can prevent the impending delivery of a shock.

Defibrillator 200 may include an internal monitoring device 281. Device 281 is called an "internal" device because it is incorporated within housing 201. Monitoring device 281 can sense or monitor patient parameters such as patient physiological parameters, system parameters and/or environmental parameters, all of which can be called patient data. In other words, internal monitoring device 281 can be complementary or an alternative to outside monitoring device 180 of FIG. 1. Allocating which of the parameters are to be monitored by which of monitoring devices 180, 281 can be done according to design considerations. Device 281 may include one or more sensors, as also described elsewhere in this document.

Patient parameters may include patient physiological parameters. Patient physiological parameters may include, for example and without limitation, those physiological parameters that can be of any help in detecting by the WCD system whether or not the patient is in need of a shock or other intervention or assistance. Patient physiological parameters may also optionally include the patient's medical history, event history and so on. Examples of such parameters include the patient's ECG, heart rate, blood oxygen level, blood flow, blood pressure, blood perfusion, pulsatile change in light transmission or reflection properties of perfused tissue, heart sounds, heart wall motion, breathing sounds and pulse. Accordingly, monitoring devices 180, 281 may include one or more sensors configured to acquire patient physiological signals. Examples of such sensors or transducers include one or more electrodes to detect ECG data, a perfusion sensor, a pulse oximeter, a device for detecting blood flow (e.g. a Doppler device), a sensor for detecting blood pressure (e.g. a cuff), an optical sensor, illumination detectors and sensors perhaps working together with light sources for detecting color change in tissue, a motion sensor, a device that can detect heart wall movement, a sound sensor, a device with a microphone, an $SpO_2$ sensor, and so on. In view of this disclosure, it will be appreciated that such sensors can help detect the patient's pulse, and can therefore also be called pulse detection sensors, pulse sensors, and pulse rate sensors, heart rate sensors, heart beat irregularity sensors, etc. In addition, a person skilled in the art may implement other ways of performing pulse detection.

In some embodiments, the local parameter is a trend that can be detected in a monitored physiological parameter of patient 282. A trend can be detected by comparing values of parameters at different times over short and long terms. Parameters whose detected trends can particularly help a cardiac rehabilitation program include: a) cardiac function (e.g. ejection fraction, stroke volume, cardiac output, etc.); b) heart rate variability at rest or during exercise; c) heart rate profile during exercise and measurement of activity vigor, such as from the profile of an accelerometer signal and informed from adaptive rate pacemaker technology; d) heart rate trending; e) perfusion, such as from $SpO_2$, $CO_2$, or other parameters such as those mentioned above, f) respiratory function, respiratory rate, etc.; g) motion, level of activity; and so on. Once a trend is detected, it can be stored and/or reported via a communication link, along perhaps with a warning if warranted. From the report, a physician monitoring the progress of patient 282 will know about a condition that is either not improving or deteriorating.

Patient state parameters include recorded aspects of patient 282, such as motion, posture, whether they have spoken recently plus maybe also what they said, and so on, plus optionally the history of these parameters. Or, one of these monitoring devices could include a location sensor such as a Global Positioning System (GPS) location sensor. Such a sensor can detect the location, plus a speed can be detected as a rate of change of location over time. Many motion detectors output a motion signal that is indicative of the motion of the detector, and thus of the patient's body. Patient state parameters can be very helpful in narrowing down the determination of whether SCA is indeed taking place.

A WCD system made according to embodiments may thus include a motion detector. In embodiments, a motion detector can be implemented within monitoring device 180 or monitoring device 281. Such a motion detector can be made in many ways as is known in the art, for example by using an accelerometer. In this example, a motion detector 287 is implemented within monitoring device 281. A motion detector of a WCD system according to embodiments can be configured to detect a motion event. A motion event can be defined as is convenient, for example a change in motion from a baseline motion or rest, etc. In such cases, a sensed patient parameter is motion.

System parameters of a WCD system can include system identification, battery status, system date and time, reports of self-testing, records of data entered, records of episodes and intervention, and so on. In response to the detected motion event, the motion detector may render or generate, from the detected motion event or motion, a motion detection input that can be received by a subsequent device or functionality.

Environmental parameters can include ambient temperature and pressure. Moreover, a humidity sensor may provide information as to whether or not it is likely raining. Presumed patient location could also be considered an environmental parameter. The patient location could be presumed, if monitoring device 180 or 281 includes a GPS location sensor as per the above, and if it is presumed that the patient is wearing the WCD system.

Defibrillator 200 typically includes a defibrillation port 210, which can be a socket in housing 201. Defibrillation port 210 includes electrical nodes 214, 218. Leads of defibrillation electrodes 204, 208, such as leads 105 of FIG. 1, can be plugged into defibrillation port 210, so as to make electrical contact with nodes 214, 218, respectively. It is also possible that defibrillation electrodes 204, 208 are connected continuously to defibrillation port 210, instead. Either way, defibrillation port 210 can be used for guiding, via electrodes, to the wearer at least some of the electrical charge that has been stored in an energy storage module 250 that is described more fully later in this document. The electric charge will be the shock for defibrillation, pacing, and so on.

Defibrillator 200 may optionally also have a sensor port 219 in housing 201, which is also sometimes known as an ECG port. Sensor port 219 can be adapted for plugging in sensing electrodes 209, which are also known as ECG electrodes and ECG leads. It is also possible that sensing electrodes 209 can be connected continuously to sensor port 219, instead. Sensing electrodes 209 are types of transducers that can help sense an ECG signal, e.g. a 12-lead signal, or a signal from a different number of leads, especially if they make good electrical contact with the body of the patient and in particular with the skin of the patient. As with defibrillation electrodes 204, 208, the support structure can be configured to be worn by patient 282 so as to maintain sensing electrodes 209 on a body of patient 282. For example, sensing electrodes 209 can be attached to the inside of support structure 170 for making good electrical contact with the patient, similarly with defibrillation electrodes 204, 208.

Optionally a WCD system according to embodiments also includes a fluid that it can deploy automatically between the electrodes and the patient's skin. The fluid can be conductive, such as by including an electrolyte, for establishing a better electrical contact between the electrodes and the skin. Electrically speaking, when the fluid is deployed, the electrical impedance between each electrode and the skin is reduced. Mechanically speaking, the fluid may be in the form of a low-viscosity gel, so that it does not flow away, after being deployed, from the location it is released near the electrode. The fluid can be used for both defibrillation electrodes 204, 208, and for sensing electrodes 209.

The fluid may be initially stored in a fluid reservoir, not shown in FIG. 2. Such a fluid reservoir can be coupled to the support structure. In addition, a WCD system according to embodiments further includes a fluid deploying mechanism 274. Fluid deploying mechanism 274 can be configured to cause at least some of the fluid to be released from the reservoir, and be deployed near one or both of the patient locations to which electrodes 204, 208 are configured to be attached to the patient. In some embodiments, fluid deploying mechanism 274 is activated prior to the electrical discharge responsive to receiving activation signal AS from a processor 230, which is described more fully later in this document.

In some embodiments, defibrillator 200 also includes a measurement circuit 220, as one or more of its modules working together with its sensors or transducers. Measurement circuit 220 senses one or more electrical physiological signals of the patient from sensor port 219, if provided. Even if defibrillator 200 lacks sensor port 219, measurement circuit 220 may optionally obtain physiological signals through nodes 214, 218 instead, when defibrillation electrodes 204, 208 are attached to the patient. In these cases, the input reflects an ECG measurement. The patient parameter can be an ECG, which can be sensed as a voltage difference between electrodes 204, 208. In addition, the patient parameter can be an impedance, which can be sensed between electrodes 204, 208 and/or between the connections of sensor port 219 considered pairwise. Sensing the impedance can be useful for detecting, among other things, whether these electrodes 204, 208 and/or sensing electrodes 209 are not making good electrical contact with the patient's body. These patient physiological signals may be sensed when available. Measurement circuit 220 can then render or generate information about them as inputs, data, other signals, etc. As such, measurement circuit 220 can be configured to render a patient input responsive to a patient parameter sensed by a sensor. In some embodiments, measurement circuit 220 can be configured to render a patient input, such as values of an ECG signal, responsive to the ECG signal sensed by sensing electrodes 209. More strictly speaking, the information rendered by measurement circuit 220 is output from it, but this information can be called an input because it is received as an input by a subsequent device or functionality.

Defibrillator 200 also includes a processor 230. Processor 230 may be implemented in a number of ways. Such ways include, by way of example and not of limitation, digital and/or analog processors such as microprocessors and Digital Signal Processors (DSPs), controllers such as microcontrollers, software running in a machine, programmable circuits such as Field Programmable Gate Arrays (FPGAs), Field-Programmable Analog Arrays (FPAAs), Programmable Logic Devices (PLDs), Application Specific Integrated Circuits (ASICs), any combination of one or more of these, and so on.

Processor 230 may include, or have access to, a non-transitory storage medium, such as memory 238 that is described more fully later in this document. Such a memory can have a non-volatile component for storage of machine-readable and machine-executable instructions. A set of such instructions can also be called a program. The instructions, which may also be referred to as "software," generally provide functionality by performing acts, operations and/or methods as may be disclosed herein or understood by one skilled in the art in view of the disclosed embodiments. In some embodiments, and as a matter of convention used herein, instances of the software may be referred to as a "module" and by other similar terms. Generally, a module includes a set of the instructions so as to offer or fulfill a particular functionality. Embodiments of modules and the functionality delivered are not limited by the embodiments described in this document.

Processor 230 can be considered to have a number of modules. One such module can be a detection module 232. Detection module 232 can include a Ventricular Fibrillation (VF) detector. The patient's sensed ECG from measurement circuit 220, which can be available as inputs, data that reflect values, or values of other signals, may be used by the VF detector to determine whether the patient is experiencing VF. Detecting VF is useful, because VF typically results in SCA. Detection module 232 can also include a Ventricular Tachycardia (VT) detector for detecting VT, and so on.

Another such module in processor 230 can be an advice module 234, which generates advice for what to do. The advice can be based on outputs of detection module 232. There can be many types of advice according to embodiments. In some embodiments, the advice is a shock/no shock determination that processor 230 can make, for example via advice module 234. The shock/no shock determination can be made by executing a stored Shock Advisory Algorithm. A Shock Advisory Algorithm can make a shock/no shock determination from one or more ECG signals that are captured according to embodiments, and determine whether or not a shock criterion is met. The determination can be made from a rhythm analysis of the captured ECG signal or otherwise. For example, there can be shock decisions for VF, VT, etc.

One more example of a decision that can be made is to bias one or more electrodes towards the person's body, as will be described later in this document. The decision can be communicated in some of these embodiments by generating a biasing signal BA. Defibrillator 300 optionally includes also a bias port 292 for exporting biasing signal BA from bias port 292 to a biasing mechanism of the system, such as biasing mechanism 194.

In some embodiments, when the determination is to shock, an electrical charge is delivered to the patient. Delivering the electrical charge is also known as discharging and shocking the patient. As mentioned above, such can be for defibrillation, pacing, and so on.

In perfect conditions, a very reliable shock/no shock determination can be made from a segment of the sensed ECG signal of the patient. In practice, however, the ECG signal is often corrupted by electrical noise, which makes it difficult to analyze. Too much noise sometimes causes an incorrect detection of a heart arrhythmia, resulting in a false alarm to the patient. Noisy ECG signals may be handled as described in U.S. patent application Ser. No. 16/037,990, filed on Jul. 17, 2018 and since published as U.S. 2019/0030351 A1, and also in U.S. patent application Ser. No. 16/038,007, filed on Jul. 17, 2018 and since published as U.S. 2019/0030352 A1, both by the same applicant and incorporated herein by reference.

Processor 230 can include additional modules, such as other module 236, for other functions. In addition, if internal monitoring device 281 is indeed provided, processor 230 may receive its inputs, etc.

Defibrillator 200 optionally further includes a memory 238, which can work together with processor 230. Memory 238 may be implemented in a number of ways. Such ways include, by way of example and not of limitation, volatile memories, Nonvolatile Memories (NVM), Read-Only Memories (ROM), Random Access Memories (RAM), magnetic disk storage media, optical storage media, smart cards, flash memory devices, any combination of these, and so on. Memory 238 is thus a non-transitory storage medium. Memory 238, if provided, can include programs for processor 230, which processor 230 may be able to read and execute. More particularly, the programs can include sets of instructions in the form of code, which processor 230 may be able to execute upon reading. Executing is performed by physical manipulations of physical quantities, and may result in functions, operations, processes, acts, actions and/or methods to be performed, and/or the processor to cause other devices or components or blocks to perform such functions, operations, processes, acts, actions and/or methods. The programs can be operational for the inherent needs of processor 230, and can also include protocols and ways that decisions can be made by advice module 234. In addition, memory 238 can store prompts for user 282, if this user is a local rescuer. Moreover, memory 238 can store data. This data can include patient data, system data and environmental data, for example as learned by internal monitoring device 281 and outside monitoring device 180. The data can be stored in memory 238 before it is transmitted out of defibrillator 200, or be stored there after it is received by defibrillator 200.

Defibrillator 200 can optionally include a communication module 290, for establishing one or more wired or wireless communication links with other devices of other entities, such as a remote assistance center, Emergency Medical Services (EMS), and so on. The communication links can be used to transfer data and commands. The data may be patient data, event information, therapy attempted, CPR performance, system data, environmental data, and so on. For example, communication module 290 may transmit wirelessly, e.g. on a daily basis, heart rate, respiratory rate, and other vital signs data to a server accessible over the internet, for instance as described in U.S. 20140043149. This data can be analyzed directly by the patient's physician and can also be analyzed automatically by algorithms designed to detect a developing illness and then notify medical personnel via text, email, phone, etc. Module 290 may also include such interconnected sub-components as may be deemed necessary by a person skilled in the art, for example an antenna, portions of a processor, supporting electronics, outlet for a telephone or a network cable, etc.

Defibrillator 200 may also include a power source 240. To enable portability of defibrillator 200, power source 240 typically includes a battery. Such a battery is typically implemented as a battery pack, which can be rechargeable or not. Sometimes a combination is used of rechargeable and non-rechargeable battery packs. Other embodiments of power source 240 can include an AC power override, for where AC power will be available, an energy-storing capacitor, and so on. Appropriate components may be included to provide for charging or replacing power source 240. In some embodiments, power source 240 is controlled and/or monitored by processor 230.

Defibrillator 200 may additionally include an energy storage module 250. Energy storage module 250 can be coupled to the support structure of the WCD system, for example either directly or via the electrodes and their leads. Module 250 is where some electrical energy can be stored temporarily in the form of an electrical charge, when preparing it for discharge to administer a shock. In embodiments, module 250 can be charged from power source 240 to the desired amount of energy, as controlled by processor 230. In typical implementations, module 250 includes a capacitor 252, which can be a single capacitor or a system of capacitors, and so on. In some embodiments, energy storage module 250 includes a device that exhibits high power density, such as an ultracapacitor. As described above, capacitor 252 can store the energy in the form of an electrical charge, for delivering to the patient.

A decision to shock can be made responsive to the shock criterion being met, as per the above-mentioned determination. When the decision is to shock, processor 230 can be configured to cause at least some or all of the electrical charge stored in module 250 to be discharged through patient 82 while the support structure is worn by patient 82, so as to deliver a shock 111 to patient 82.

For causing the discharge, defibrillator 200 moreover includes a discharge circuit 255. When the decision is to shock, processor 230 can be configured to control discharge circuit 255 to discharge through the patient at least some of all of the electrical charge stored in energy storage module 250. Discharging can be to nodes 214, 218, and from there to defibrillation electrodes 204, 208, so as to cause a shock to be delivered to the patient. Circuit 255 can include one or more switches 257. Switches 257 can be made in a number of ways, such as by an H-bridge, and so on. Circuit 255 could also be thus controlled via processor 230, and/or user interface 280.

A time waveform of the discharge may be controlled by thus controlling discharge circuit 255. The amount of energy of the discharge can be controlled by how much energy storage module has been charged, and also by how long discharge circuit 255 is controlled to remain open.

Defibrillator 200 can optionally include other components.

In a number of embodiments, the ECG electrodes are not always making good electrical contact with the patient's skin. In fact, a certain one of these ECG electrodes can be coupled to the support structure such that, while the support structure is worn by the patient, the certain ECG electrode is at a so-called unbiased state. When in the unbiased state, the certain ECG electrode is moveable with respect to the patient's body, for example as a result of the patient's moving around. For example, the certain ECG electrode could contact the patient's skin as a regular garment does, for example as does a shirt that is not tightened around the patient's body. As such the certain ECG electrode could shift around the patient's skin, and occasionally lose contact with it. In those occasional moments, the electrical impedance between the certain ECG electrode and the patient's skin would become infinite. Of course, what is written about the certain ECG electrode could also apply for companions electrodes that performs a similar function.

It is that lack of the certain ECG electrode's making consistently good electrical contact with the skin that makes the support structure more comfortable to wear for the long term. Of course, the certain ECG electrode not necessarily making consistently good electrical contact for the long term is not desirable, but that will be addressed by the biasing mechanism that is now described.

Embodiments of the system of the invention may additionally include a biasing mechanism. The biasing mechanism can be configured to cause the certain ECG electrode to transition from the above described unbiased state to a so-called biased state. When in the biased state, the certain ECG electrode is biased towards the patient's body against the support structure. The biasing, then, is by a force that causes the certain ECG electrode to be less moveable with respect to the patient's body than when in the unbiased state. As such, when in the biased state, the certain ECG electrode makes better and/or more reliable electrical contact with the patient's skin than in the unbiased state. The better electrical contact can be used for more reliable defibrillation and or receiving ECG signals, as the case may be for the certain ECG electrode.

In preferred embodiments, the biasing mechanism can cause the certain ECG electrode to transition from the unbiased state to the biased state, responsive to a monitoring condition being met. As such, the biasing mechanism can be configured to receive a biasing signal that signifies that the determination has been made that the monitoring condition has been met. For example, when a logic device has been provided to make that determination, the biasing mechanism can be configured to receive the biasing signal from that logic device. An example was described above for biasing signal BA.

The transitioning from the biased state to the unbiased state is also called biasing and deployment of the certain ECG electrode. Deployment is for the certain ECG electrode, and possibly also other electrodes of the system. It will be appreciated that deployment in this sense might not necessarily change much the position of the certain ECG electrode with respect to the patient's body, but it will change the force with which it is pushed or biased towards the body.

The biasing mechanism can be made in any way so as to cause pressure to be applied to the certain ECG electrode against the support structure, and therefore bias the certain ECG electrode towards the patient's body. Various embodiments of the biasing mechanism include a spring that is released, causing the support structure to be tightened around the body, causing a balloon to be inflated, adding pressure to a hydraulic system, applying force such as with an electromagnet, turning a screw gun arrangement so that turning result in a translation motion, and or tightening a belt around the body that makes multiple such ECG electrodes come in better contact with the body.

A sample deployment is now described. FIG. 3A is a diagram according to an embodiment. A patient 382 is wearing a support structure 370, of which two portions are shown. Support structure 370 is made according to embodiments and, as with FIG. 1, two parts of it are indicated only generically. A certain ECG electrode 309 is coupled to support structure 370 in an unbiased state. In the instant of FIG. 3A, certain ECG electrode 309 does not even contact the skin of patient 382. A biasing mechanism 394 is also coupled to support structure 370.

FIG. 3B is a diagram showing the same elements as FIG. 3A, except that biasing mechanism 394 exerts a biasing force 396 due to which certain ECG electrode 309 is biased towards patient 382 against support structure 370. In the instant of FIG. 3B, certain ECG electrode 309 contacts the skin of patient 382. Certain ECG electrode 309 is less easily movable in FIG. 3B than in FIG. 3A.

In a number of embodiments the biasing mechanism is preferably made so that it is further reversible, either by the wearer, or by a bystander, or by a remotely monitoring medical professional. Reversing could be upon verifying that there is no actionable episode to be addressed by the system. Reversing could be automatically enabled by further functionality. Or, reversing could be implemented by permitting the mechanically reverse motion of what deployed the certain ECG electrode and any other electrodes. Care should be taken that reversing is not suggested prematurely, or by a patient who does not understand the function of the system, such as a well-meaning by uninformed bystander.

It will be appreciated that, when the certain ECG electrode is in the biased state, it can be counted on to make better electrical contact with the body. Accordingly, any ECG inputs received by the certain ECG electrode preferably are trusted more when the certain ECG electrode is in the biased state than in the unbiased state. Regardless, in a preferred embodiment, an additional, serendipitous check on the patient can be an ECG reading that is received incidentally while the certain ECG electrode is in the unbiased state and whose content causes alarm. Such an ECG reading can be used in a number of ways.

Figure 4:
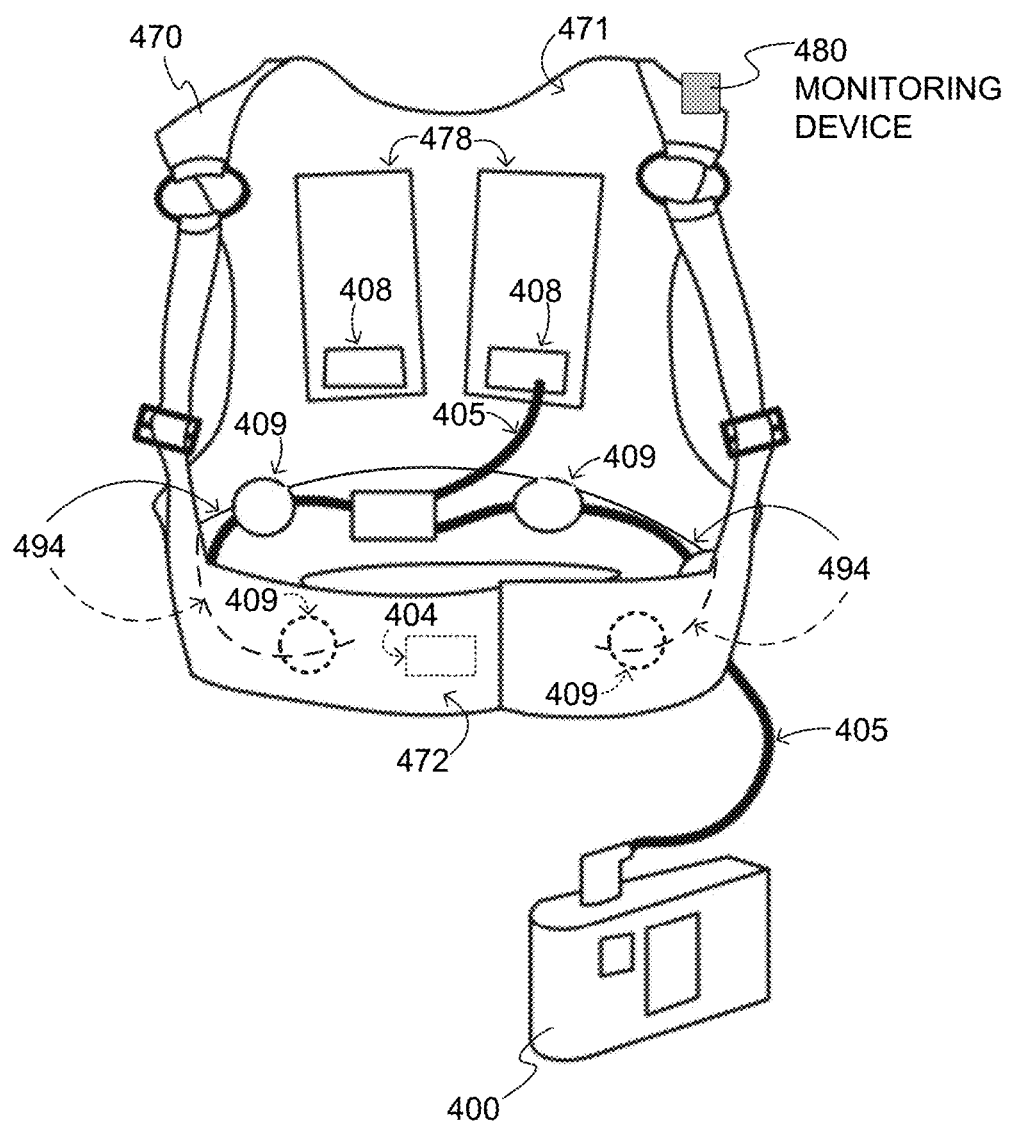
FIG. 4 is a diagram of sample embodiments of components of a WCD system.

FIG. 4 is a diagram of sample embodiments of components of an WCD system. A support structure 470 includes a flexible vest-like wearable garment. Support structure 470 has a back side 471, and a front side 472 that closes in front of the chest of the patient.

The WCD system of FIG. 4 also includes an external defibrillator 400. FIG. 4 does not show any support for external defibrillator 400, which may be carried in a purse, on a belt, by a strap over the shoulder, and so on. Wires 405 connect external defibrillator 400 to electrodes 404, 408, 409. Of those, electrodes 404, 408 are defibrillation electrodes, and electrodes 409 are ECG sensing electrodes.

Support structure 470 is configured to be worn by the ambulatory patient so as to maintain electrodes 404, 408, 409 on a body of the patient. Indeed, back defibrillation electrodes 408 are maintained in pockets 478. Of course, the inside of pockets 478 can be made with loose netting, so that electrodes 408 can contact the back of the patient, especially with the help of the conductive fluid that has been deployed. In addition, sensing electrodes 409 are maintained in positions that surround the patient's torso, for sensing ECG signals and/or the impedance of the patient.

Moreover, a biasing mechanism includes a string 494, which is preferably provided near, and in fact behind ECG electrodes 409. String 494 may be provided wholly within vest 470, so as not to interfere with the user. The two ends of it can be attached to the garment, preferably near where the garment secures in the front. A mechanism, not shown, may tighten string 494, which biases ECG electrodes 409 inwards towards the body of the patient.

Furthermore, a monitoring device 480 may be provided for the patient, in connection with the system. Such a monitoring device 480 can be as described for the non-ECG parameters of the patient described in connection with devices 180, 281.

ECG signals in a WCD system may include too much electrical noise to be useful. To ameliorate the problem, multiple ECG electrodes 409 are provided, for presenting many ECG sensing options to processor 230. These options are different vectors for sensing the ECG signal, as described now in more detail.

Figure 5:
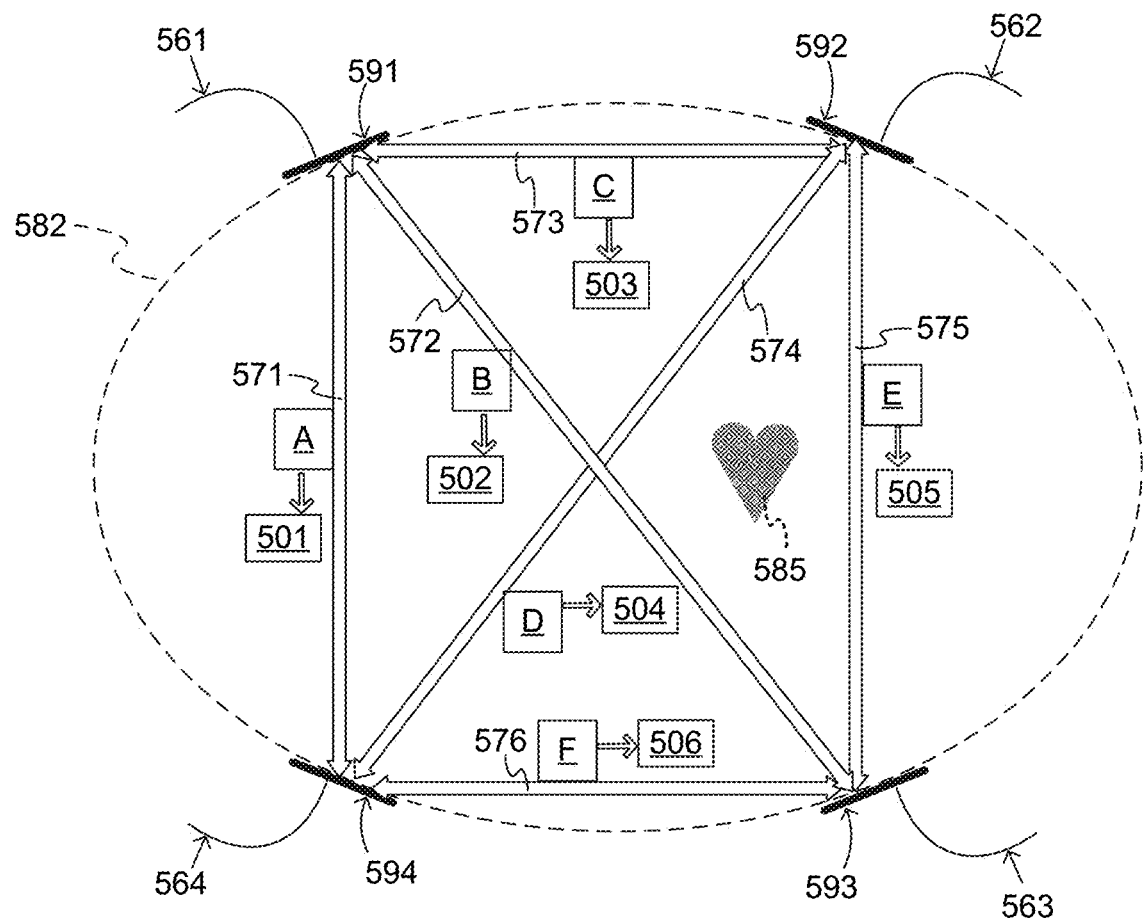
FIG. 5 is a conceptual diagram for illustrating an example how multiple electrodes may be used for sensing ECG signals along different vectors in a WCD system according to embodiments.

FIG. 5 is a conceptual diagram for illustrating how multiple electrodes of a WCD system may be used for sensing ECG signals along different vectors according to embodiments. A section of a patient 582 having a heart 585 is shown. In FIG. 5, patient 582 is viewed from the top, patient 582 is facing downwards, and the plane of FIG. 5 intersects patient 582 at the torso of the patient.

Four ECG sensing electrodes 591, 592, 593, 594 are maintained on the torso of patient 582, and have respective wire leads 561, 562, 563, 564. It will be recognized that electrodes 591, 592, 593, 594 surround the torso, similarly with ECG electrodes 409 in the example of FIG. 4.

Any pair of these four ECG sensing electrodes 591, 592, 593, 594 defines a vector, along which an ECG signal may be sensed and/or measured. As such, electrodes 591, 592, 593, 594 define six vectors 571, 572, 573, 574, 575, 576. FIG. 5 thus illustrates a multi-vector embodiment.

These vectors 571, 572, 573, 574, 575, 576 define channels A, B, C, D, E, F respectively. Concurrent ECG signals 501, 502, 503, 504, 505, 506 may thus be sensed and/or measured from channels A, B, C, D, E, F, respectively, and in particular from the appropriate pairings of wire leads 561, 562, 563, 564 for each channel.

In FIG. 5 it will be understood that ECG electrodes 591, 592, 593, 594 are drawn as being on the same plane for simplicity and as is preferred, while that is not necessarily the case. Accordingly, vectors 571, 572, 573, 574, 575, 576 are not necessarily on the same plane, either.

In embodiments, in order to make the shock/no-shock determination as correctly as possible, a WCD may assess which of ECG signals 501, 502, 503, 504, 505, 506 is best for rhythm analysis and interpretation. For example, ECG signals that have the most noise may be ignored, discarded, not considered, while leaving the remaining ECG signals as candidates for making the shock/no shock determination.

Figure 6:
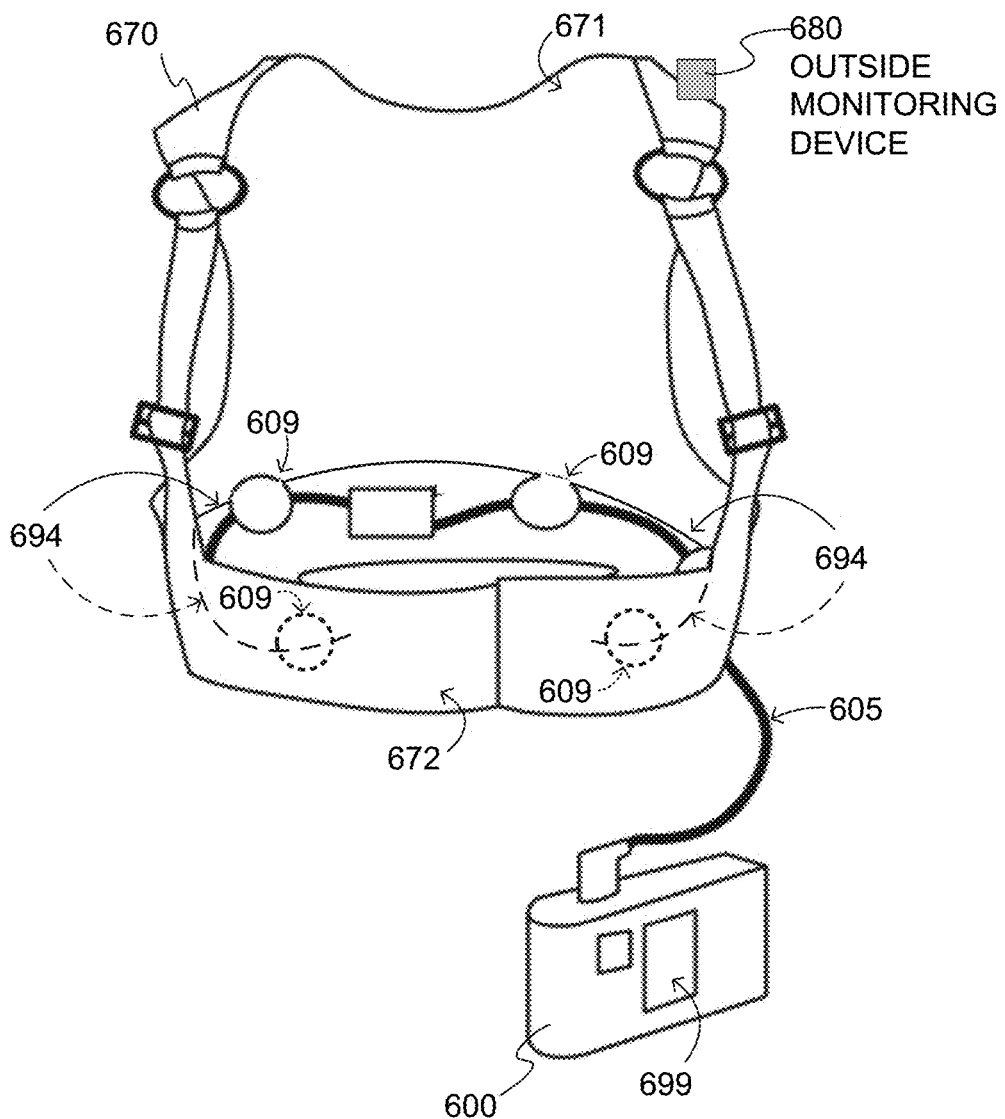
FIG. 6 is a diagram of components of a WM system made according to embodiments.

In some embodiments, a wearable medical (WM) system (WMS) has aspects similar to those of a WCD system, except it does not include the defibrillator and the defibrillator electrodes. For example, FIG. 6 is a diagram of sample embodiments of components of an WM system. Of course, a WCD system according to embodiments is also a type of a wearable medical monitor system.

In FIG. 6, a support structure 670 includes a vest-like wearable garment. Support structure 670 has a back side 671, and a front side 672 that closes in front of the chest of the patient.

The WM system of FIG. 6 also includes a device 600. FIG. 6 does not show any support for device 600, which may be carried in a purse, on a belt, by a strap over the shoulder, and so on, or on support structure 670. Wires 605 connect device 600 to ECG electrodes 609.

Support structure 670 is configured to be worn by the ambulatory patient so as to maintain ECG sensing electrodes 609 on a body of the patient. In addition, ECG sensing electrodes 609 are maintained in positions that surround the patient's torso. The ECG electrodes thus define two or more channels and are configured to sense two or more versions of an ECG signal of the patient across the two or more channels. Moreover, a biasing mechanism includes a string 694, similarly with string 494.

Device 600 may have a WM processor and a memory such as was described for processor 230 and memory 238. As such, device 600 could also be storing WM system data that is generated from samples taken during at least one hour of the sensed ECG signal. This stored WM system data can be about patient 82, according to embodiments.

Device 600 may also have a screen 699, which can be an output device of a user interface (UI). Screen 699 can also be an input device of the UI if it is a touchscreen. In some embodiments, all the processing is done by the WM processor, and the results and graphs are displayed in screen 699.

Furthermore, a monitoring device 680 may be provided for the patient, in connection with the system. Such a monitoring device 680 can be as described for the non-ECG parameters of the patient described in connection with devices 180, 281.

A number of embodiments monitor a patient for deterioration of their ECG signal, which could be due to an ailment developing over some time. In such embodiments, a memory of the WM system may store a reference template that is made from one or more early portions of the ECG signal of the ambulatory patient that are sensed during a first time duration. Later, while the patient is monitored, a test portion of the ECG signal may be input, and compared against the reference template. In some of these embodiments, the WM system is actually a wearable cardioverter defibrillator (WCD) system, which also includes one or more defibrillation electrodes that the support structure further maintains on the patient's body. Such a WCD system also includes an energy storage module that store an electrical charge, which is discharged via the defibrillation electrodes through the patient. Some of these embodiments are now described.

Figure 7:
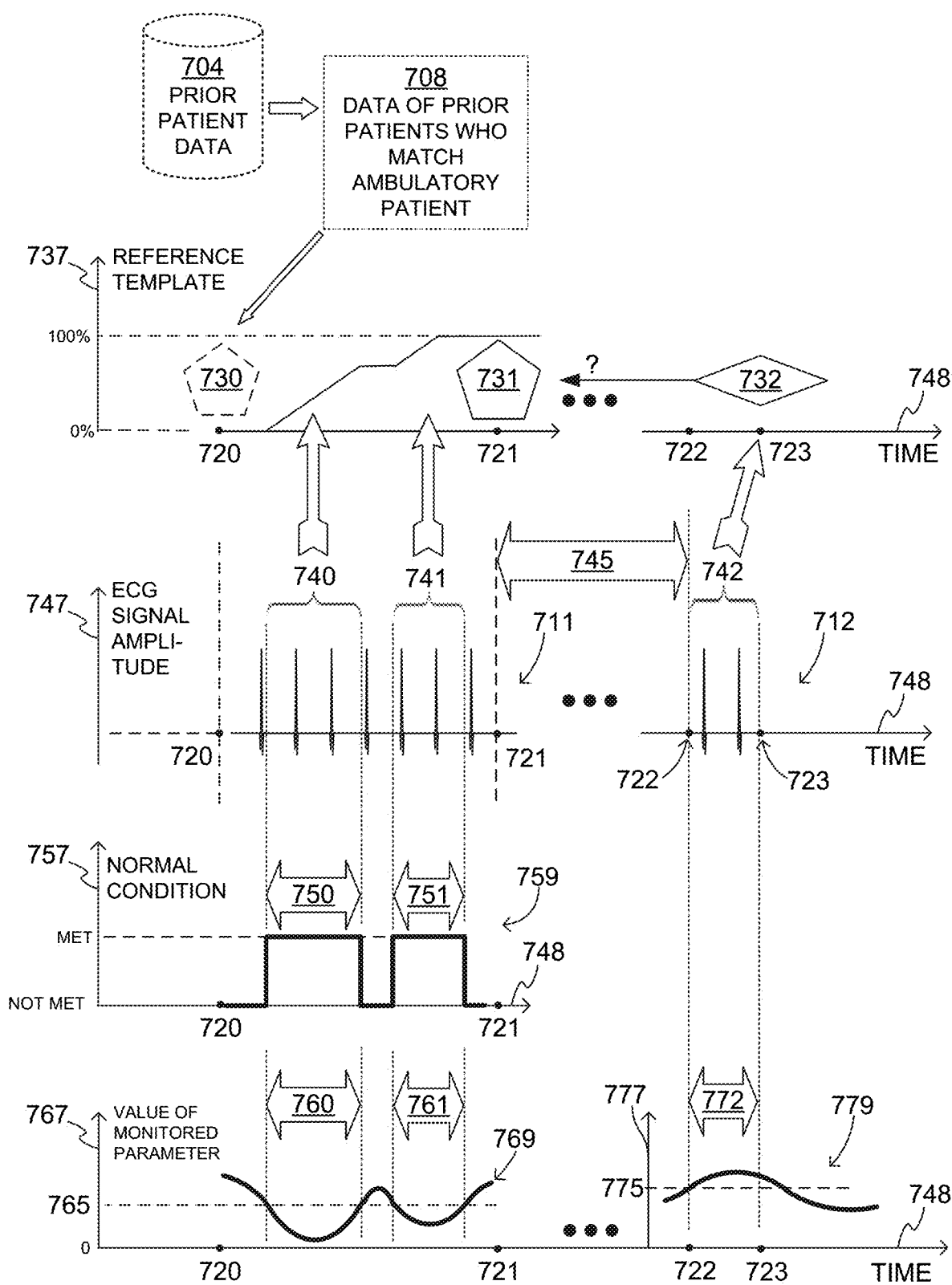
FIG. 7 shows multiple related diagrams, including time diagrams of a patient's early ECG signals that are used for creating a reference template, and of later, test ECG signals that are compared against the reference template, and also for conditions for selecting waveform segments to generate the reference template, and conditions for later causing the comparison, made according to embodiments.

FIG. 7 shows multiple diagrams and relationships among them. In about the middle of the diagram, against a vertical axis 747, the ECG signal amplitude is plotted over a time axis 748 that is discontinued in one place. Two portions of the ECG signal amplitude are plotted, namely an early portion 711 and a later portion 712.

Early portion 711 is sensed within a first time duration. The first time duration is defined, in this example, as occurring between time intercepts 720 and 721. Later portion 712 is sensed within a second time duration. The second time duration is defined as occurring between time intercepts 722 and 723. The second time duration occurs after the first time duration. In fact, the second time duration can start at least 10 min or longer after the first time duration ends. In other words, the duration between time intercepts 721 and 722, which is also shown by an arrow 745, is at least 10 min. This duration can be minutes, hours, days, weeks and months, as the patient is monitored for the long term, and much longer than what happens during the first or second time duration. This is why time axis 748 is shown discontinued for the time duration of arrow 745.

In this example, the ECG signal of early portion 711 is used to make a reference template 731. The state of completion of reference template 731 is shown conceptually against a vertical axis 737, over time axis 748 that is repeated from the diagram immediately below. In this diagram the completion is shown as rising gradually from 0% to 100%, but that is for illustrating the concept only. In embodiments, and as will be seen below the rise is not gradual. When there are enough number of normal QRS beats in a time interval, then reference template 731 can be formulated. It will be appreciated that, when the first time duration is complete at time intercept 721, reference template 731 is complete, having reached a state of completion of 100%. Then, at time intercept 723, a comparison operation 732 may be made. The comparison may be of a test portion 742 of ECG signal 712 that is sensed during second time duration 742 against reference template 731. Examples of such a comparison are given later in this document.

Returning to reference template 731, it will be appreciated that it was created with portions 740, 741 of ECG signal 711, during the first time duration. However, a system according to embodiments might not always start with a reference template 731, which has been made from the patient's data. In some embodiments, a default template 730 is optionally stored in the memory of the WM system before reference template 731 is made or completed. In such embodiments, default template 730 can be used instead of reference template 731. In particular, comparison operation 732 may determine a difference by comparing the value of the test aspect of the inputted test portion 712 of the ECG signal with a value of the reference aspect of default template 730 instead of with the value of the reference aspect of reference template 731.

In such embodiments, default template 730 may have been constructed from prior data of prior patients, such as may be in a database 704. In some of these embodiments, prior data 708 is selected from database 704, to be from prior patients who match the ambulatory patient in at least one demographic parameter of a set that includes: gender, age, height, weight, and so on. It should be noted that ECG data can be different in some aspects if they are sourced from a standard "12-lead" measurement, than if they are sourced from ECG electrodes of the type shown in FIGS. 4-6.

Making or constructing reference template 731 is now described in more detail.

Figure 8:
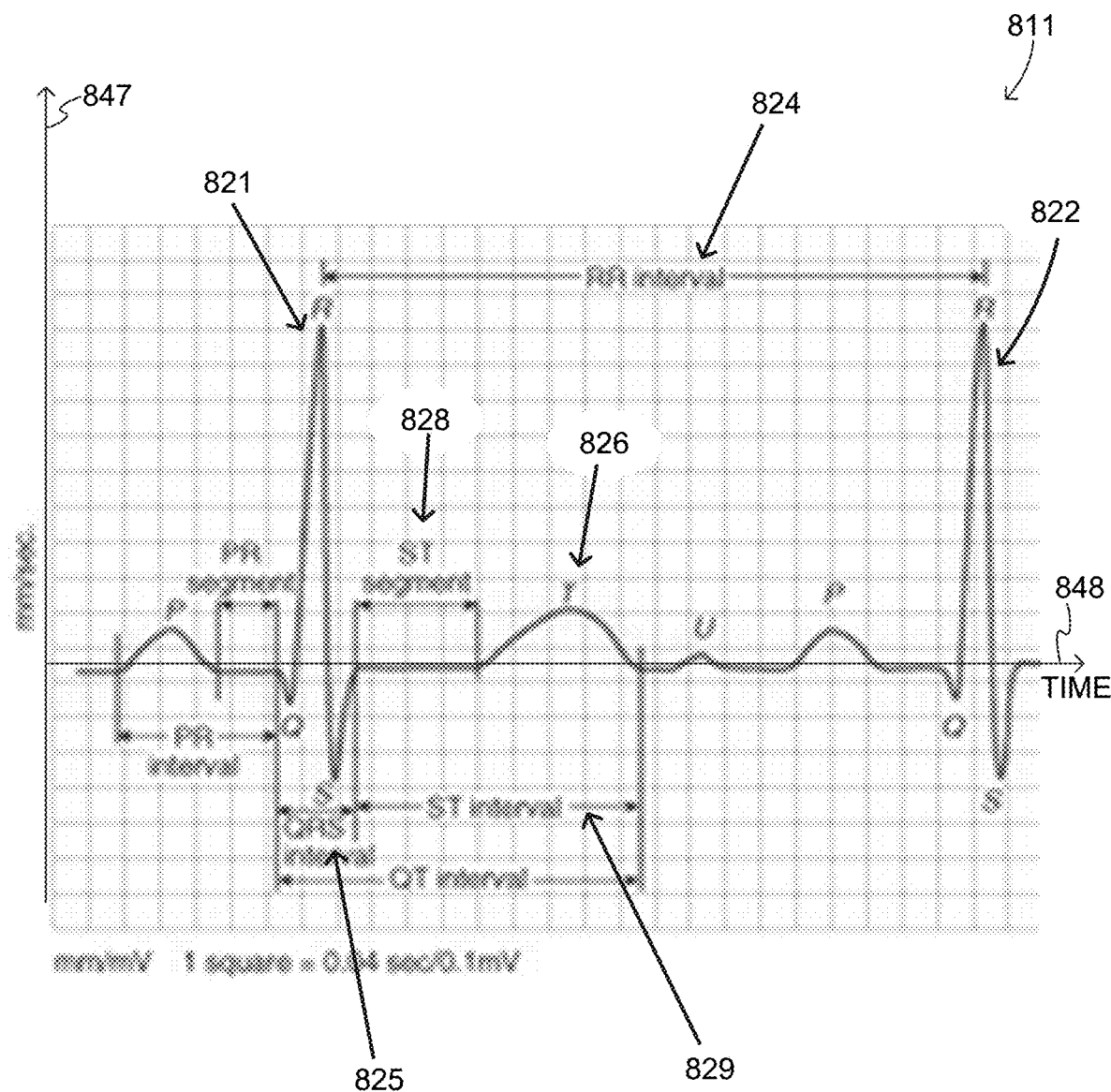
FIG. 8 is a time diagram of a segment of a waveform amplitude of an ideal ECG signal, further indicating aspects that can be monitored by embodiments.

In some embodiments, the processor of the WM system is further configured to select an amplitude waveform of a certain one of the one or more early portions 711 of the ECG signal, and store the selected amplitude waveform in the memory as the reference template. For example, FIG. 8 is a time diagram 811 of a segment of a waveform amplitude of an ideal ECG signal, assuming the patient had one that was captured this way. A non-ideal, and more usual, ECG signal amplitude waveform 1211 is also shown in a later drawing, but for a different purpose. Even if the patient's signal is not ideal, FIG. 8 serves well to indicate aspects that can be monitored according to embodiments of operation 732. The ECG amplitude waveform is shown against a vertical axis 847, and over a time axis 848. Two QRS peaks 821, 822 are included. Aspects that can be monitored according to embodiments, such as test aspects and reference aspects, include an RR interval 824, a QRS interval 825, a T-wave duration 826, an ST segment duration 828 and an ST interval duration 829. These aspects can have values given, for example, by their intercepts on axes 847, 848. In each case, the portion of the waveform stored as the reference template is chosen according to the aspect that it is desired to monitor. Of course, more than one aspects may be thus monitored according to embodiments, and so on.

In other embodiments, reference template 731 is made or constructed using multiple waveforms, in which case it can also be called a composite amplitude waveform. In particular, the processor of the WM system can be further configured to generate such a composite amplitude waveform from early amplitude waveforms of respective ones of early portions 740, 741 of the ECG signal. The composite amplitude waveform can be generated by any number of techniques, such as adding, averaging, choosing by median, a combination of such techniques, and so on. The processor can then store the composite amplitude waveform in the memory as reference template 730. Again, if multiple aspects of the signal are to be thus monitored, then reference template 730 may have multiple aspects, each with one or more values, and so on.

In some of these embodiments, the composite amplitude waveform can be generated from early amplitude waveforms that are similar to each other. The similarity can be at least in the aspects mentioned above in FIG. 8, and also in other aspects. In fact, the similarity can be quantified as internal correlation, to indicate how well-correlated are these amplitude waveforms. For example, a processor of the WM system can be further configured to identify similarity statistics of early amplitude waveforms of respective ones of the early portions of the ECG signal. Then the composite amplitude waveform can be generated from those of the early amplitude waveforms whose similarity statistics exceed a threshold.

In some of these embodiments, the processor is further configured to align the early amplitude waveforms, before generating the composite amplitude waveform from them. Aligning can help with the resulting composite amplitude waveform being a better answer. Filtering can be performed in a number of ways. One such example is by a bandpass filter. Such a filter may pass frequencies from 8 Hz to 25 Hz.

Figure 9:
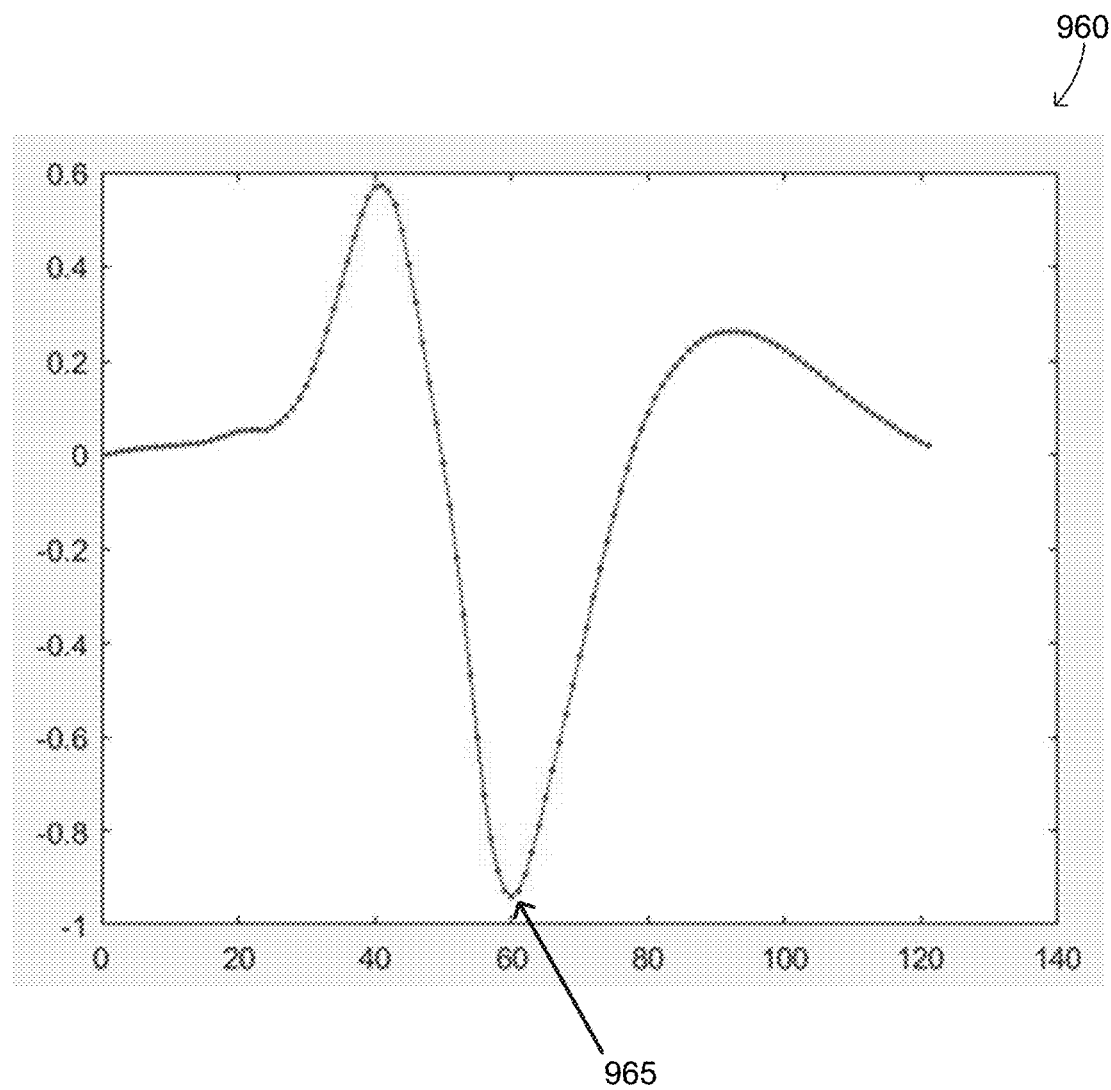
FIG. 9 is a time diagram of a sample ECG waveform that has been filtered so that it can be aligned with others according to embodiments.

In some of these embodiments, the processor is further configured to filter the early amplitude waveforms prior to aligning them. Filtering can help with the alignment, as it may sharpen a peak. An example is seen in FIG. 9, which shows a time diagram 960 of a sample ECG waveform that has been filtered. Alignment can be by aligning the early amplitude waveforms by their sharp peak 965.

The devices and/or systems mentioned in this document may perform functions, processes, acts, operations, actions and/or methods. These functions, processes, acts, operations, actions and/or methods may be implemented by one or more devices that include logic circuitry. A single such device can be alternately called a computer, and so on. It may be a standalone device or computer, such as a general-purpose computer, or part of a device that has and/or can perform one or more additional functions. The logic circuitry may include a processor and non-transitory computer-readable storage media, such as memories, of the type described elsewhere in this document. Often, for the sake of convenience only, it is preferred to implement and describe a program as various interconnected distinct software modules or features. These, along with data are individually and also collectively known as software. In some instances, software is combined with hardware, in a mix called firmware.

Moreover, methods and algorithms are described below. These methods and algorithms are not necessarily inherently associated with any particular logic device or other apparatus. Rather, they are advantageously implemented by programs for use by a computing machine, such as a general-purpose computer, a special purpose computer, a microprocessor, a processor such as described elsewhere in this document, and so on.

This detailed description may include flowcharts, display images, algorithms, and symbolic representations of program operations within at least one computer readable medium. An economy may be achieved in that a single set of flowcharts can be used to describe both programs, and also methods. So, while flowcharts describe methods in terms of boxes, they may also concurrently describe programs.

Figure 10:
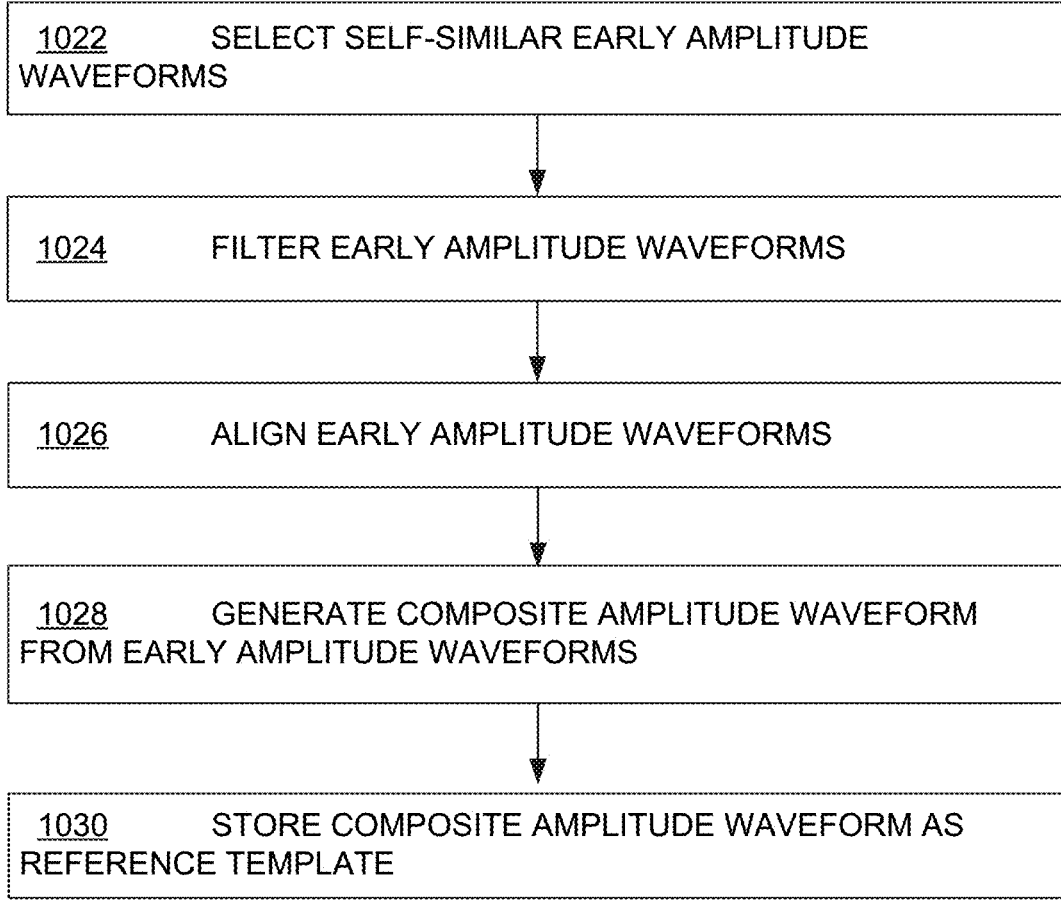
FIG. 10 is a flowchart for illustrating additional sample methods for constructing a reference template according to embodiments.

FIG. 10 shows a flowchart 1000 for describing methods according to embodiments. According to an optional operation 1022, self-similar early waveforms may be selected. These early waveforms can be amplitude waveforms. The selection may be performed, for example, by identifying similarity statistics of early amplitude waveforms of respective ones of the early portions of the ECG signal, and selecting those of the early amplitude waveforms whose similarity statistics exceed a threshold.

According to another, optional operation 1024, early amplitude waveforms may be filtered.

According to another, optional operation 1026, the early amplitude waveforms may be aligned, meaning shifted along the time axis. Shifting can be so that one of their key features matches, such as sharp peak 965.

According to another, optional operation 1028, a composite amplitude waveform may be generated from the early amplitude waveforms.

According to another, optional operation 1030, the composite amplitude waveform may be stored in the memory as the reference template.

Returning to FIG. 7, it will be appreciated that, in this example, reference template 731 was completed with contributions of only ECG signal portions 740, 741, and not from other portions of the ECG signal of the first time duration. This refinement is not required, but is preferred, to favor using ECG segments during condition that are regarded as normal. For example, in some embodiments, a processor of the WM system is further configured to determine whether or not a normal condition was met when a certain one of the early portions of the ECG signal was sensed. In such embodiments, the early amplitude waveform of the certain early portion is used to generate the composite amplitude waveform, responsive to determining that the certain early portion was sensed when a normal condition was met. If, however, the normal condition was not met, that early amplitude waveform might not be used to generate the composite amplitude waveform.

An example is seen in FIG. 7, where a vertical axis 757 is used to denote two values, namely normal condition met and not met. In this example, a plot 759 plots the evolution of that value over time axis 748. Plot 759 indicates that the normal condition is met only during time intervals 750 and 751. It will be appreciated that these time intervals 750 and 751 are what define ECG portions 740 and 741 of the diagram immediately above.

The normal condition can be defined in a number of ways. For one example, the normal condition may include that a heart rate of the patient is less than a heart rate threshold. A good heart rate threshold may be 80 bpm (beats per minute). For another example, the normal condition may include that QRS complexes appear normally, and so on. Moreover, it may be desirable to set the normal condition when the patient is sleeping, or in a supine position but not sleeping, or sitting, or standing still, which can be confirmed with a variety of sensors, such as sound sensors, motion sensors, a clock input and so on.

In some such embodiments, the WM system may further include a monitoring device configured to monitor at least one physiological parameter of the ambulatory patient that is not the ECG signal of the ambulatory patient. In such embodiments, the normal condition is met responsive to a value of the monitored parameter being less than a normal threshold. An example is seen in FIG. 7 by a plot 769. The value of such a monitored parameter is tracked against a vertical axis 767 over time axis 748. Plot 769 indicates that the normal condition is met only during time intervals 760 and 761, because that is when a normal threshold 765 is not exceeded. It will be appreciated that these time intervals 760 and 761 are what created plot 759 immediately above, and therefore defined ECG portions 740 and 741 of the diagram further above.

The physiological parameter that is monitored can be any one of the patient's heart rate, blood perfusion, blood flow, blood pressure, blood oxygen level, pulsatile change in light transmission or reflection properties of perfused tissue, heart sounds, breathing sounds, pulse, and motion. Accordingly, a monitoring device of the WM system can include a sensor, for detecting when the condition is normal. The sensor can be appropriate for sensing and producing a value for the physiological parameter that is being monitored.

Figure 11:
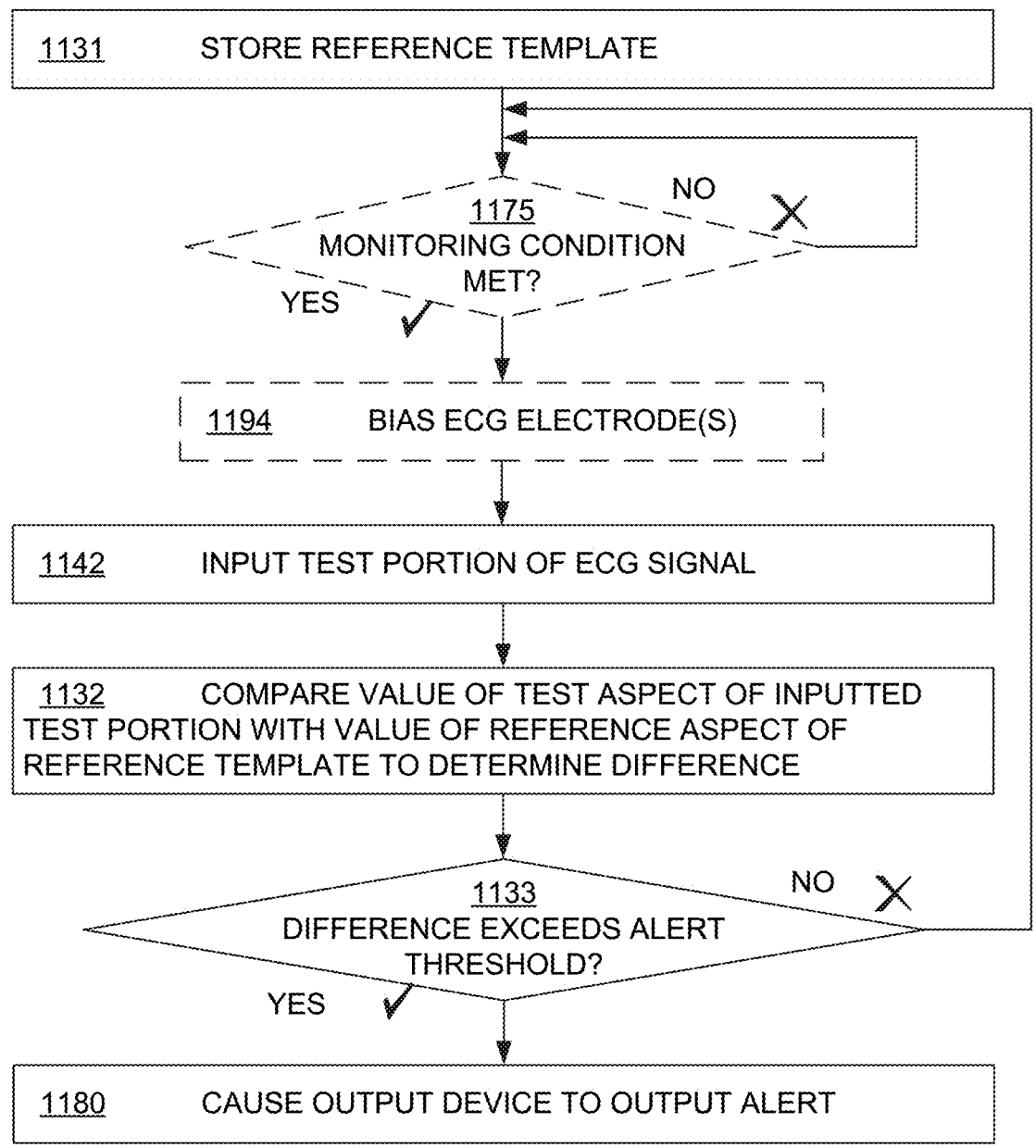
FIG. 11 is a flowchart for illustrating sample methods according to embodiments.

FIG. 11 shows a flowchart 1100 for describing methods according to embodiments. According to an operation 1131, a reference template may be stored in a memory of the WM system.

According to another, optional operation 1175, it may be determined whether or not a monitoring condition is met. Examples are given elsewhere in this document. If not, then operation 1175 may be performed again, perhaps after some delay.

If yes then, according to another, optional operation 1194, ECG electrodes may be biased towards the patient. This can be performed in a number of ways. For example, a certain one of the ECG electrodes may be caused, by biasing mechanism 194, 394, to transition from the unbiased state to the biased state. In addition, this biasing may also take place for the first time period, when the normal condition is met. After being performed, the biasing may be later reversed to relieve the patient, and so on.

According to another operation 1142, a test portion of the ECG signal may be input. Such a test portion maybe sensed during a second time duration that starts at least 10 min after the first time duration ends. Inputting may be by sensing from the patient, or by recalling a signal stored in the memory.

According to another operation 1132, a value of a test aspect of the inputted test portion may be compared with a value of a reference aspect of the reference template stored in the memory, to determine a difference. This is similar to operation 732. In addition, waveforms of the test portion of the ECG signal may be aggregated for the comparison. As such, the test aspect may include an aggregated waveform of the test portion of the ECG signal.

According to another operation 1133, it is determined whether the difference determined at operation 1132 exceeds an alert threshold. If not, then execution may return to an earlier operation such as operation 1175.

If yes then, according to another operation 1180, an output user interface device can be caused to output an alert.

Monitoring conditions, such as of operation 1175, can be similar to what was described for determining whether or not a normal condition is met. For example, the WM system may further include one or more monitoring devices, such as those described in connection with determining whether or not a normal condition is met. These monitoring devices can now determine instead whether or not a monitoring condition is met. The monitoring condition is not necessarily the same as the normal condition.

An example is seen in FIG. 7 by a plot 779. The value of such a monitored parameter is tracked against a vertical axis 777 over time axis 748. Plot 779 indicates that the monitoring condition is met only during time interval 772, because that is when plot 779 exceeds monitoring threshold 775. It will be appreciated that this time interval 772 is what defined ECG portion 742 of the diagram above.

It will be further observed that monitoring threshold 775 does not necessarily have the same value as normal threshold 765. In case where they are both heart rate thresholds, monitoring threshold 775 could be set at a suitable value, such as 90 bpm.

Another example is when the processor further includes a clock configured to keep a time. The monitoring condition can be met responsive to the time reaching a checking moment. One more example is when the WM system further includes a user interface (UI) having an input device that is configured to be actuated by the patient. The monitoring condition may be met responsive to the patient actuating the input device on his own.

Figure 12:
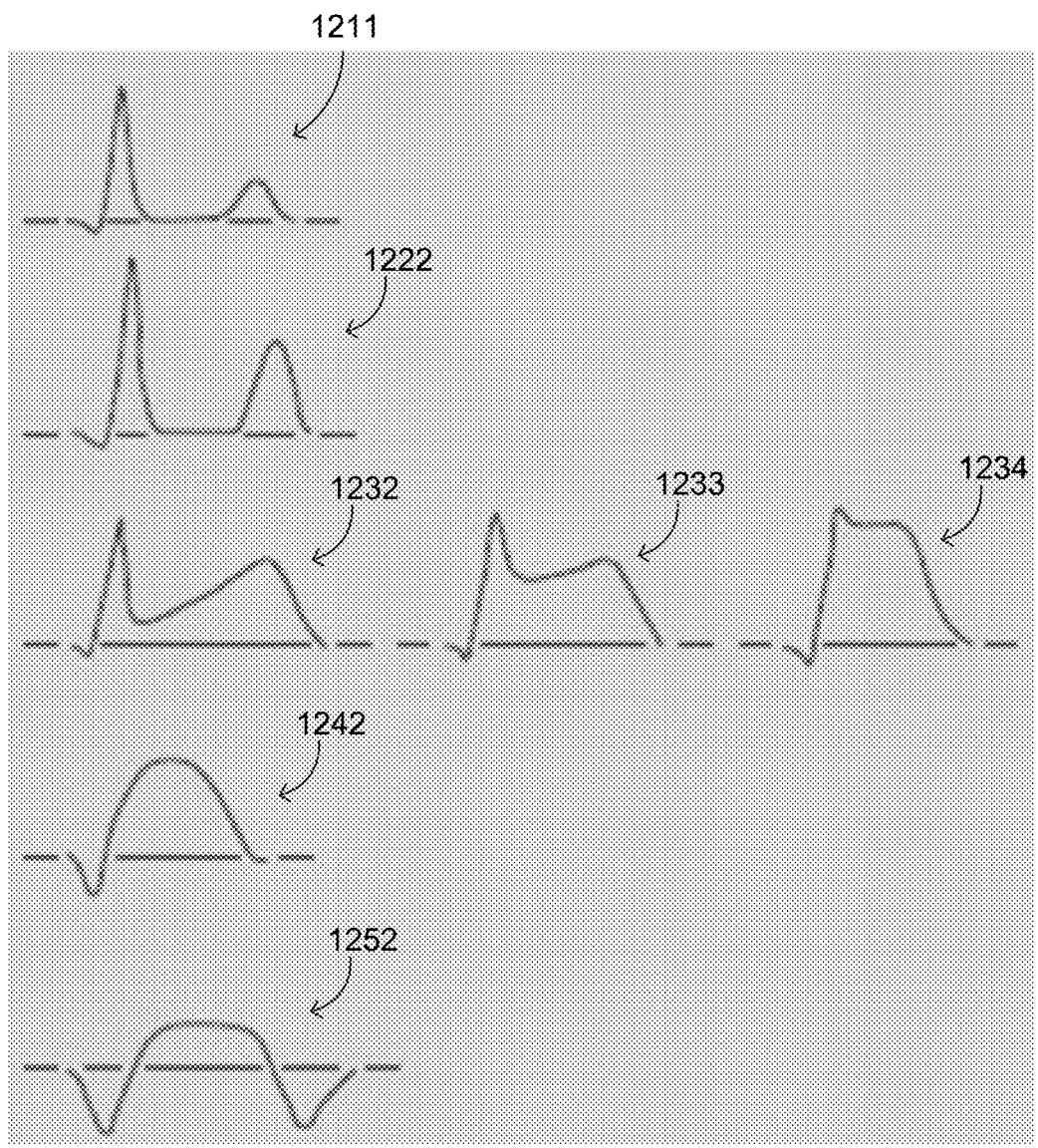
FIG. 12 shows sample time diagrams of a healthy and of suspect ECG waveforms that can be detected by embodiments.

FIG. 12 shows sample time diagrams of a healthy and of suspect ECG waveforms that can be detected by embodiments. Waveform 1211 is deemed as a relatively healthy one, where a QRS peak is followed by a T-wave. Waveform 1211 is presented also for easier contrast with other waveforms in this diagram, which are not as healthy. Indeed, waveform 1222 exhibits a peaked T-wave, while waveforms 1232, 1233, 1234 exhibit increasing degrees of ST segment elevation. Waveform 1242 exhibits Q wave formation and loss of R wave, while waveform 1252 exhibits T-wave inversion.

Unhealthy waveforms, such as those of FIG. 12, may be detected by a suitable choice of the test aspect. For example, the test aspect may include a QRS interval of a QRS complex of the inputted test portion. Or, the test aspect may include an ST segment or an ST interval after a QRS complex of the inputted test portion. Or, the test aspect may include a T-wave after a QRS complex of the inputted test portion. In these instances, the choice of the test aspect indicates the corresponding choice of the reference aspect. Detection can be facilitated by aligning waveforms as mentioned above, and then examining a difference in other aspects.

In some embodiments, the difference of operation 1132 is determined by computing a waveform similarity coefficient. In such embodiments, the alert can be output responsive to the computed waveform similarity coefficient being below a similarity threshold.

In some of these embodiments, the waveform similarity coefficient is computed according to equation 1377 in FIG. 13 of this document. In equation 1377, FCC stands for feature correlation coefficient. Its value ranges from 1, which amounts to perfect correlation, to 0, which means complete lack of correlation. As an aside, such an FCC statistic can also be used to measure the stability and self-similarity of the early waveforms that constitute the reference template. A good value for N can be chosen depending on the sampling rate and the QRS-T duration. In some embodiments, a value of about 8 points works well. Examples of using the FCC are now described.

Figure 14A:
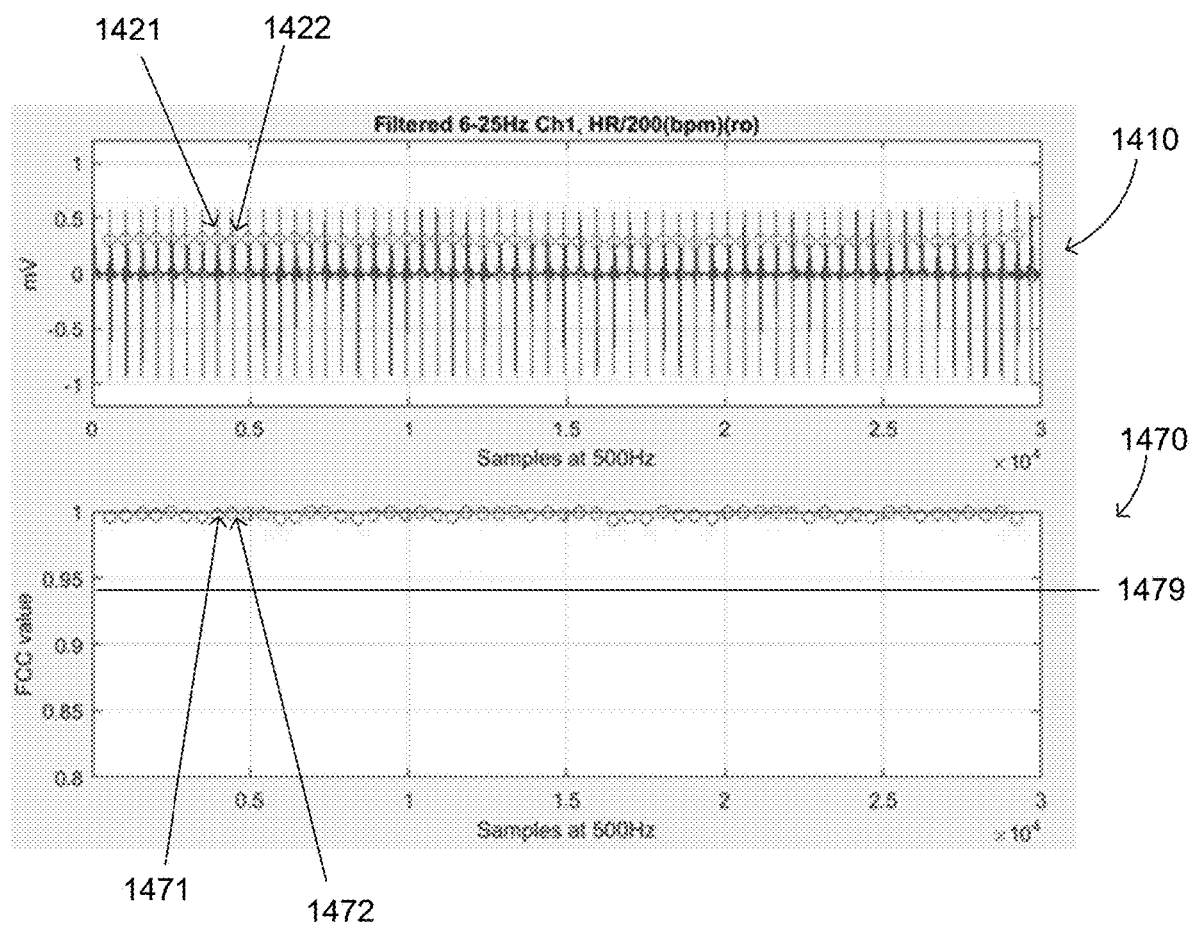
FIG. 14A shows a first time diagram of an ECG signal with detected QRS peaks, and a second time diagram showing computed waveform similarity coefficients for the peaks, according to embodiments.

FIG. 14A shows a time diagram of an ECG signal 1410, with QRS peaks that appear to the human eye as parallel vertical lines. Little circles 1421, 1422 indicate where QRS peaks have been detected. ECG signal 1410 is taken during a patient's regular heartbeat.

FIG. 14A also shows another time diagram 1470, on the same time axis as ECG signal 1410. Second time diagram 1470 plots the waveform similarity coefficients for the peaks detected in the above diagram, which have been computed according to equation 1377 in FIG. 13. Of those, two sample coefficients 1471, 1472 are shown, which correspond to QRS peaks 1421, 1422 respectively. It will be appreciated that, in this example, all coefficients are above a threshold line 1479, which corresponds to a value of 0.94. In fact, all are much higher, all much closer to 1 and all rather similar to each other. As such, ECG signal 1410 is rather well-correlated. A metric can be established suitably for quantifying this internal correlation.

The waveforms of ECG signal 1410 may be aggregated, for example by extracting an average. Given the sampling rate of 500 Hz, the shown 30,000 samples of ECG signal 1410 would give about 60 sec of signal, which is adequate for aggregating. For averaging, prior to adding the waveforms are preferably aligned, and prior to aligning they are first filtered, as described above at least in FIG. 10.

Figure 14B:
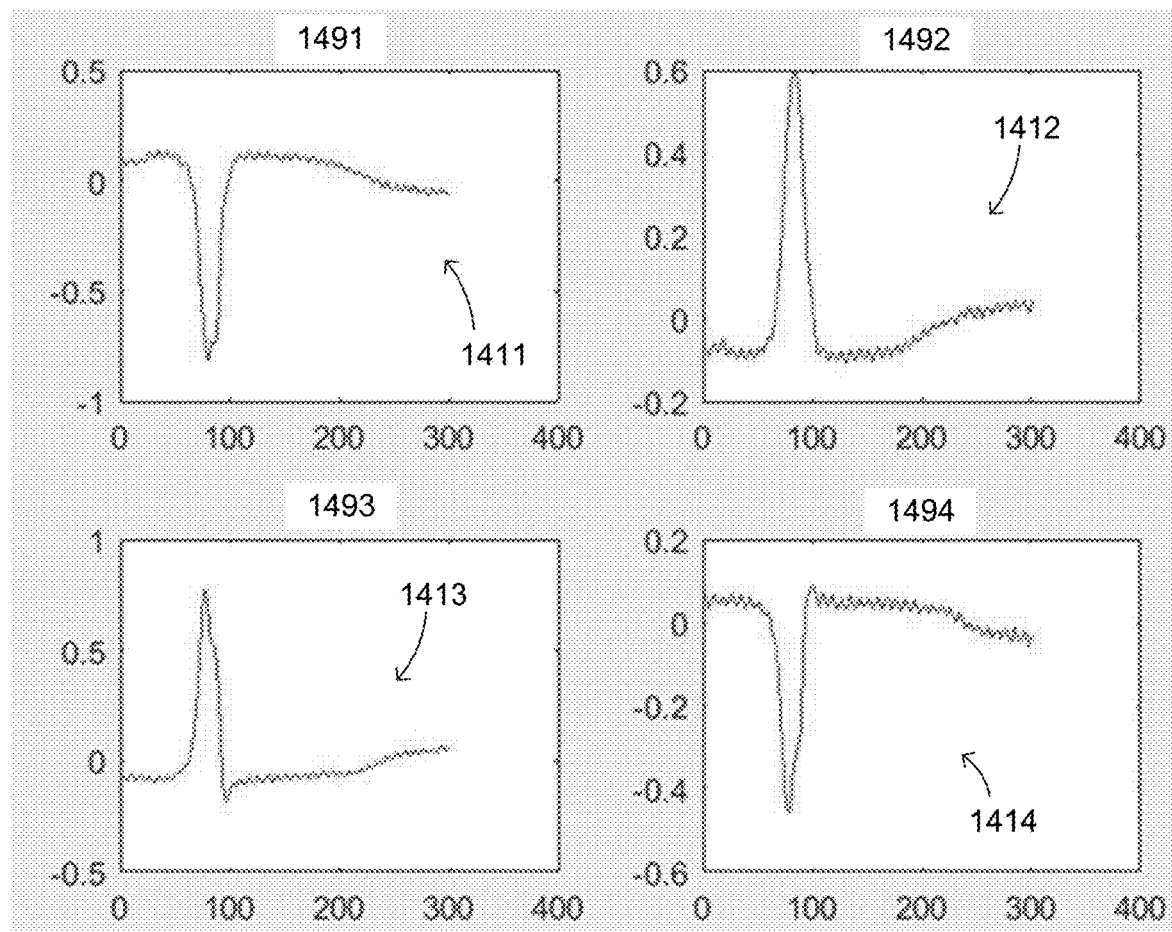
FIG. 14B shows aggregated signals that could be made from the ECG signals of FIG. 14A, according to embodiments.

The aggregated waveforms can form an average QRS_T waveform of each unfiltered ECG signal. The results are shown in FIG. 14B, which shows sample concurrent aggregated signals 1411, 1412, 1413, 1414, after removing the DC offset. These aggregated signals correspond to ECG electrodes 1491, 1492, 1493, 1494, and are with respect to common reference voltage, and are thus also called single-ended. ECG electrodes 1491, 1492, 1493, 1494 could be, for example ECG electrodes 591, 592, 593, 594. The signal from the channel, however, would be by taking a difference of these signals. Aggregated signals 1411, 1412, 1413, 1414 can also be used as reference templates, one for the signal of each electrode, or the difference of two per channel. If a prior reference template had been stored but was not well-correlated internally, then signals 1411, 1412, 1413, 1414 can serve as an updated reference template, which is better correlated. In other words, a previous template may have been stored in the memory, before the new reference template is made from aggregated signals 1411, 1412, 1413, 1414. The previous template may have a first metric of internal correlation, but the new reference template may have a second metric of internal correlation. The previous template may be replaced thus by the new reference template responsive to the second metric exceeding the first metric.

Figure 15A:
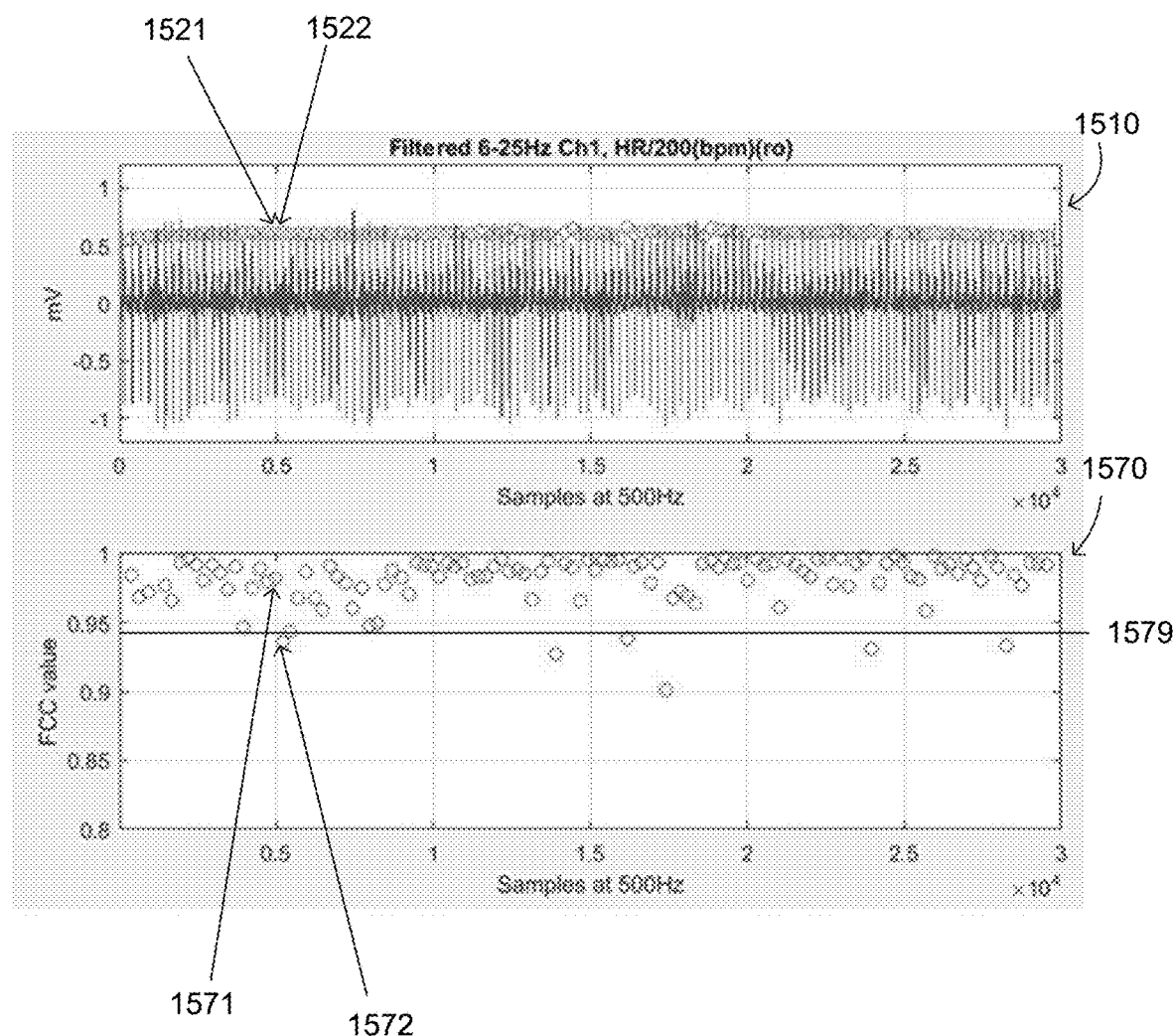
FIG. 15A shows a first time diagram of an ECG signal with detected QRS peaks, and a second time diagram showing computed waveform similarity coefficients for the peaks, according to embodiments.

FIG. 15A shows a time diagram of an ECG signal 1510, with QRS peaks that appear to the human eye as parallel vertical lines. Little circles 1521, 1522 indicate where QRS peaks have been detected. ECG signal 1510 is taken during a patient's elevated heart rate of around 120 bpm.

FIG. 15A also shows a time diagram 1570, on the same time axis as ECG signal 1510. Second time diagram 1570 plots the waveform similarity coefficients for the peaks detected in the above diagram, which have been computed according to equation 1377 in FIG. 13. Of those, two sample coefficients 1571, 1572 are shown, which correspond to QRS peaks 1521, 1522 respectively. In this example, coefficient 1572 is not above a threshold line 1579, which corresponds to a value of 0.94. As such, ECG signal 1510 is less well-correlated internally than ECG signal 1410.

Figure 15B:
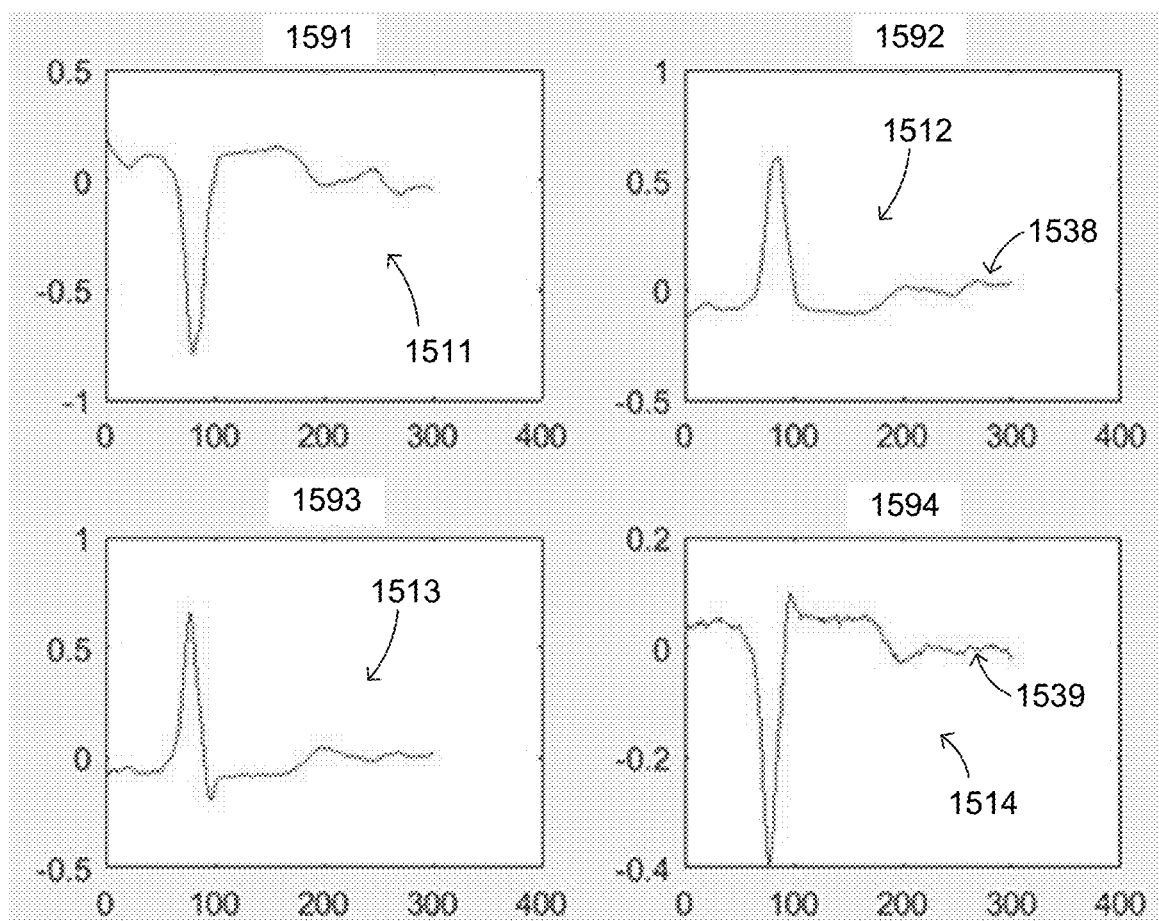
FIG. 15B shows aggregated signals that could be made from the ECG signals of FIG. 15A, according to embodiments.

The waveforms of ECG signal 1510 may be aggregated, for example by extracting an average, as with FIGS. 14A, 14B. The results are shown in FIG. 15B, which shows sample concurrent aggregated signals 1511, 1512, 1513, 1514, after removing the DC offset. These aggregated signals correspond to ECG electrodes 1591, 1592, 1593, 1594, and are with respect to common reference voltage. ECG electrodes 1591, 1592, 1593, 1594 could be, for example ECG electrodes 591, 592, 593, 594, or even 1491, 1492, 1493, 1494 but at a later time than in FIG. 14A.

If aggregated signals 1411, 1412, 1413, 1414 had become stored as the reference templates, and aggregated signals 1511, 1512, 1513, 1514 are compared to them as later test portions, the FCC may have been used for computing the difference for operation 1132. In such a case, ECG signal 1510 is a test portion of the ECG signal, and aggregated signals 1512, 1514 are test aspects of it. The difference for operation 1132 includes new features 1538, 1539. They correspond to a T-wave variation relative to the reference templates, which can happen when the heart is stressed. Such stress to the heart may happen during an activity such as running, shoveling snow, etc. The ST segment can change, by being elevated or depressed, which can be a heart attack symptom. As such, the patient and/or a clinician may be notified, and the patient may stop the activity, if that were the problem. Of course, ST segment changes can occur during a myocardial infarction/heart attack independently of the patient's activity. Plus, activity-induced ST segment changes can be indicative of an issue other than heart attack, such as such as coronary spasm.

In some embodiments, the processor is further configured to store in the memory an event responsive to the difference exceeding the alert threshold. This way, the event may be reviewed later.

The alert of operation 1180 may be output in a number of ways. In some embodiments, the WM system includes a user interface (UI), and the output device belongs to the UI. In such embodiments, the alert is output by the output device emitting a human-perceptible indication, such as a sound, a light, a vibration, and so on.

In other embodiments, the WM system includes a communication module that is the output device. In such embodiments, the alert is output by the communication module transmitting a notification to another device, such as a computer, a telephone, and so on, for example for a remote person to react.

In some embodiments, the memory of the WM system further stores a table that lists a plurality of possible ailments of the ambulatory patient. Such ailments may include a higher heart rate, a caution about a possible heart attack, decompensation, stroke, and heart failure or the possibility of the onset of heart failure. For example, reference templates may be stored for such ailments, comparisons can be made for matching such ailments, and so on.

A number of embodiments monitor a patient for a myocardial infarction (MI), such as an acute MI (AMI), by monitoring primarily a physiological parameter of the patient that is not the ECG signal of the patient. In such embodiments, a memory of the WM system may store one or more myocardial infarction (MI) alarm conditions that are related to an MI. While the patient is monitored, a value of the monitored physiological parameter is input, and it is determined whether or not that value meets at least one of the one or more MI alarm conditions. In some of these embodiments, the system is also a wearable cardioverter defibrillator (WCD) system, which also includes one or more defibrillation electrodes that the support structure further maintains on the patient's body. Such a WCD system also includes an energy storage module that store an electrical charge, which is discharged via the defibrillation electrodes through the patient. Some of these embodiments are now described.

Figure 16:
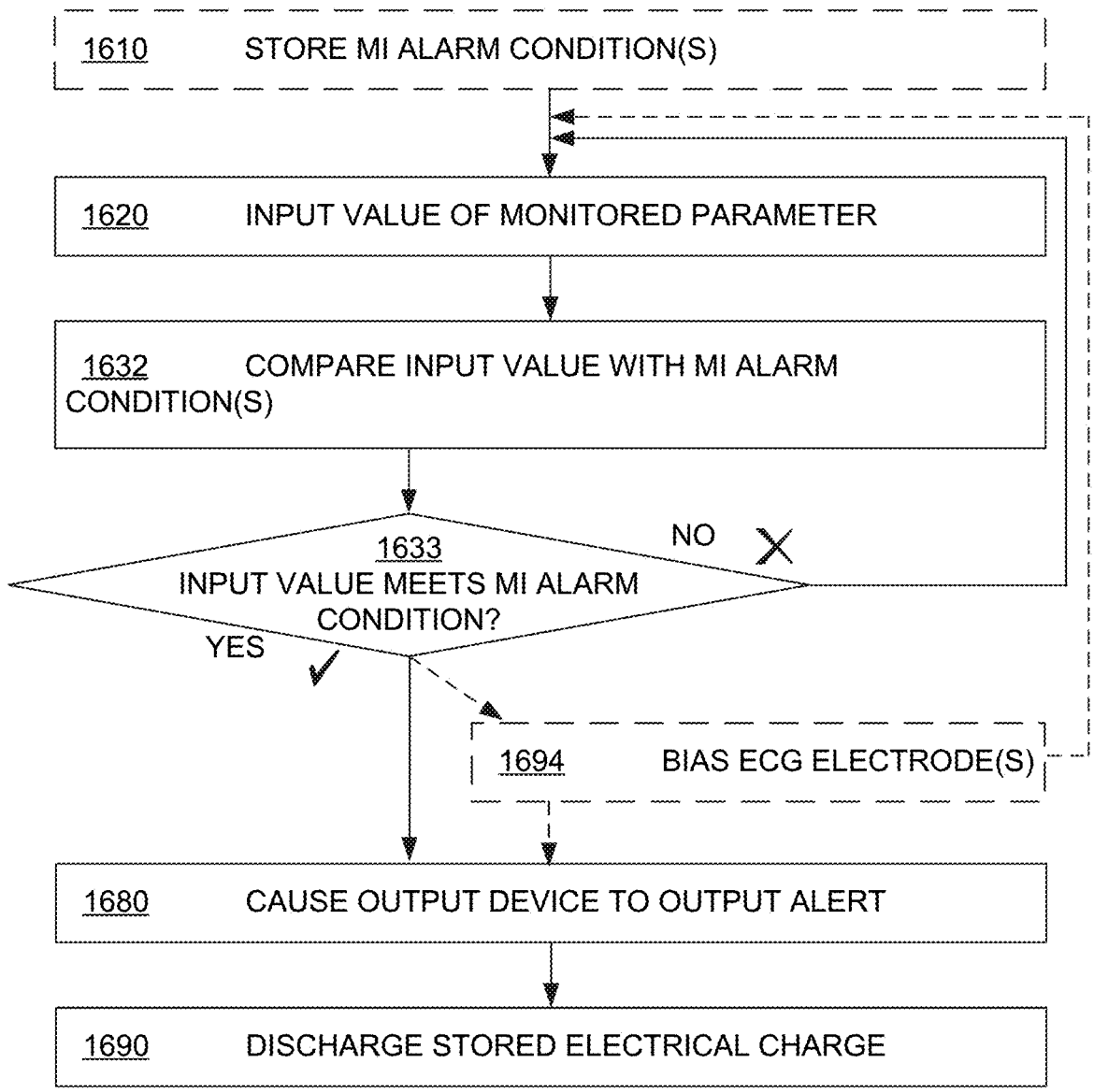
FIG. 16 is a flowchart for illustrating sample methods according to embodiments.

FIG. 16 shows a flowchart 1600 for describing methods according to embodiments.

According to an optional operation 1610, myocardial infarction (MI) alarm conditions are stored, for example in a memory of the WM system. These MI alarm conditions may be related to a myocardial infarction, and further be chosen according to the physiological parameter that is monitored. These MI alarm conditions can be generated as described later in this document.

According to another operation 1620, a value of a monitored physiological parameter may be input. This physiological parameter need not be the ECG signal of the patient, and examples are described elsewhere in this document.

According to another operation 1632 the input value may be compared with the stored MI alarm conditions.

According to another operation 1633, it may be determined, as a result of operation 1632, whether or not the input value meets at least one of the stored one or more MI alarm conditions. If not, then execution may exit, or return to an earlier operation such as operation 1620.

If at operation 1633 the answer is yes, there are two options, depending on whether or not optional operation 1694 is provided for, and/or performed. If not optional operation 1694 is not performed or provided for then, according to another operation 1680, an output device is caused to output an alert. This may be performed, for example, similarly with operation 1180 of FIG. 11. According to another, optional operation 1690, a stored electrical charge may be discharged via a defibrillation electrode through the ambulatory patient.

In some of these embodiments, the WM system further includes electrocardiogram (ECG) electrodes that are configured to be maintained on a body of the ambulatory patient by the support structure. In such embodiments, the ECG electrodes can be configured, when thus maintained, to sense an ECG signal of the ambulatory patient. This ECG signal may provide additional information about a possible MI.

In some of these embodiments, a biasing mechanism is provided, similarly with what was described above. In such embodiments, optional operation 1694 in FIG. 16 can be provided for and performed, responsive to a condition. Such a condition can be any suitable condition of the type described above, such as a monitoring condition and/or determining that the input value meets at least one of the one or more MI alarm conditions at operation 1633. Then ECG electrodes may be biased towards the patient, similarly with operation 1194. Additional operations may then occur similarly with previous embodiments, ultimately leading to operation 1680 or 1620. In particular, a reference template can be further stored in the memory, and a test portion of the ECG signal of the ambulatory patient can be input that is thus sensed by the certain ECG electrode in the biased state. Then a test aspect of the inputted test portion can be compared with a reference aspect of the stored reference template to determine a difference, and the output device can be caused to output an alert responsive to the difference exceeding an alert threshold.

In some of these embodiments, the monitored physiological parameter of the patient includes one or more of heart sounds, a breathing sound, a heart rate, a pulsatile blood flow, a blood oxygen level, a blood perfusion, a change in light transmission or reflection properties of perfused tissue, a color of a skin, and a motion.

For each such monitored physiological parameter, the monitoring device may be made accordingly, with appropriate sensors. A WM system according to embodiments may have one or more types of sensors, and one or more sensors of each type. Outputs of such sensors, and of monitoring devices, may be used individually, or together for higher confidence.

For each type of monitored physiological parameter, the corresponding MI alarm conditions can be generated in relation to the parameter, for example as logical rules for a processor of the WM system. In particular, it can be identified what aspect of the each of the parameters signifies a possible MI.

For example, the monitoring device may include a perfusion detector. Such a perfusion detector may monitor blood perfusion of the patient, and detect perfusion, heart beats, heart beat rate, heart beat intensity, heart beat consistency, etc. The corresponding MI alarm conditions can be generated when these detected quantities are not normal, for example rapid heartbeats (frequency higher than a threshold), irregular heartbeats (a custom statistic about regularity not meeting a threshold), etc.

For another example, the monitoring device may include a microphone. Such a microphone can be configured to monitor the patient's heart sounds and/or breathing sounds, by appropriate placement etc.

For heart sounds, the microphone may detect frequency, volume, intensity, regularity, etc. of heart beats. Again, the corresponding MI alarm conditions can be generated accordingly.

For breathing sounds, the microphone may detect frequency, volume, regularity, etc. of breaths. Again, the corresponding MI alarm conditions can be generated accordingly. For example, a frequency that is too high may indicate shortness of breath. The breathing sounds can also be used for detection of snoring, especially if coupled with confirming indications of conditions related to snoring, such as perhaps ambient light being low, time being that of the night, motion sensors indicating no other motion, and so on.

Figure 17A:
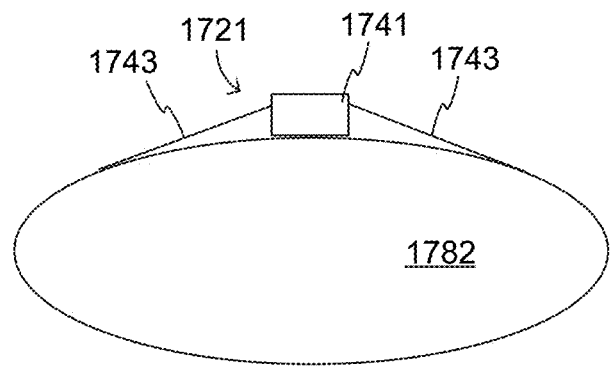
FIG. 17A is a diagram of a sample breathing sensor according to embodiments.

FIG. 17A is a diagram of a breathing sensor 1721 made according to embodiments, which is being used by a patient 1782, seen from the top. A section view of the torso of patient 1782 is shown. Breathing sensor 1721 has a sensor housing 1741 that is held against the torso by a band 1743. Band 1743 may be long enough to form an entire loop be around the chest of patient 1782. Alternately, a remainder of the loop may be formed by one or more other members, which may be elastic or not. The patient's breathing thus may stretch and release the band with respect to housing 1741. This stretching and releasing may be detected in a number of ways, and an example is now described.

Figure 17B:
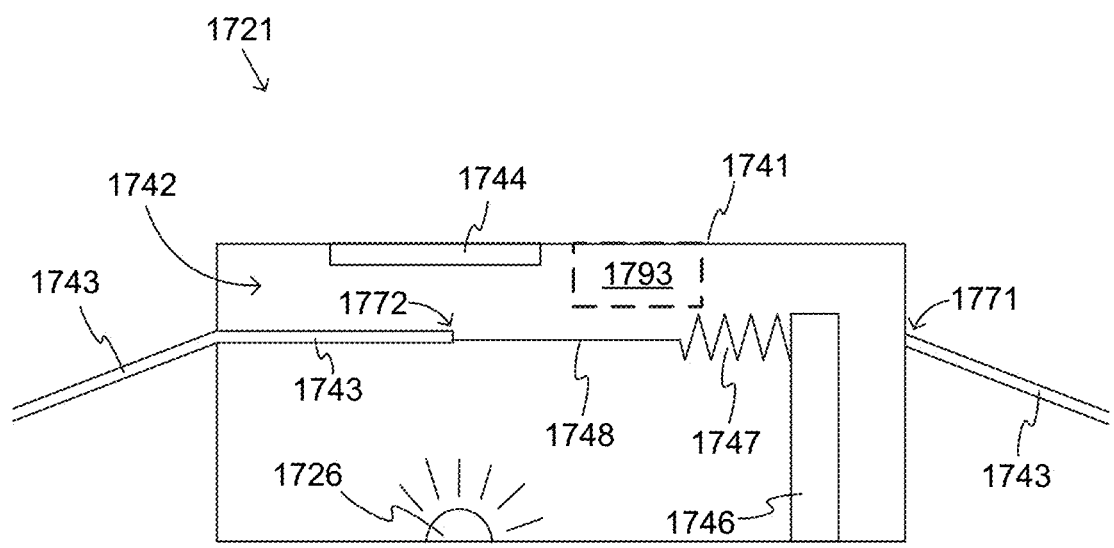
FIG. 17B is a diagram of a detail of a sample embodiment of the breathing sensor of FIG. 17A.

FIG. 17B is a diagram of a detail of a sample embodiment of the sensor module of FIG. 17A. In this example, band 1743 has two ends 1771, 1772 attached to sensor housing 1741, and sensor housing 1741 is thus pressed towards the chest of the patient by the stretching of band 1743. Sensor housing 1741 has a cavity 1742, and end 1772 reaches within sensor housing 1741. In addition, breathing sensor 1721 includes a spring 1747 that is coupled to end 1772, for example via a thread 1748. Accordingly, spring 1747 keeps band 1743 stretched against a fixed post 1746. The patient's breathing causes end 1772 to oscillate from left to right and back again. Band 1743 may be elastic in case breathing exceeds the stretching range of spring 1747.

The oscillation of end 1772 can be detected in a number of ways. In the example of FIG. 17B, a light source 1726 can project light that can be imaged by imager 1744. Imager 1744 can be a pixel array, a small linear array of larger photodetectors, and so on. It helps if band 1743 is wide and end 1772, while thread 1748 is thin, so that end 1772 will cast a shadow, helping imager 1744 detect better. Stretching and releasing band 1743 will move end 1772 left and write, changing where the shadow is case on imager 1744. If higher detection sensitivity is desired, end 1772 may be moved lower within the housing so that it is closer to light source 1726 than is suggested by the diagram, so that the left-ward move caused by an inhalation of the patient will remove more shadow from imager 1744.

In other embodiments, a camera can be used to image end 1772, and detect any movement, although such requires a software application to detect. For using a camera, a light source may be required to illuminate end 1772, perhaps from a different angle than shown in the example of FIG. 17B.

Breathing sensor 1721 may also include a communication device 1793 and other components.

A drawback in detecting breathing is that some people breathe only lightly in the first place. It may be helpful to have a calibration procedure for determining how patient 1782 breathes, at what times, etc.

For another example, the monitoring device may include a sweat sensor, which can be configured to monitor sweating of the ambulatory patient. A number of sweat sensors are possible, for example as described in the following US patent documents: U.S. 20090269003, U.S. 20170100102, U.S. 20170238854, U.S. Pat. No. 7,383,072, U.S. 20060253011, U.S. 20180160951, U.S. Pat. No. 9,828,060, U.S.20190008383, U.S. 20170101158, U.S. 20180263538, U.S. 20170095183 and U.S. 20170079574. In addition, another embodiment of a sweat detector is now described, which uses a hygrometer.

Figure 18:
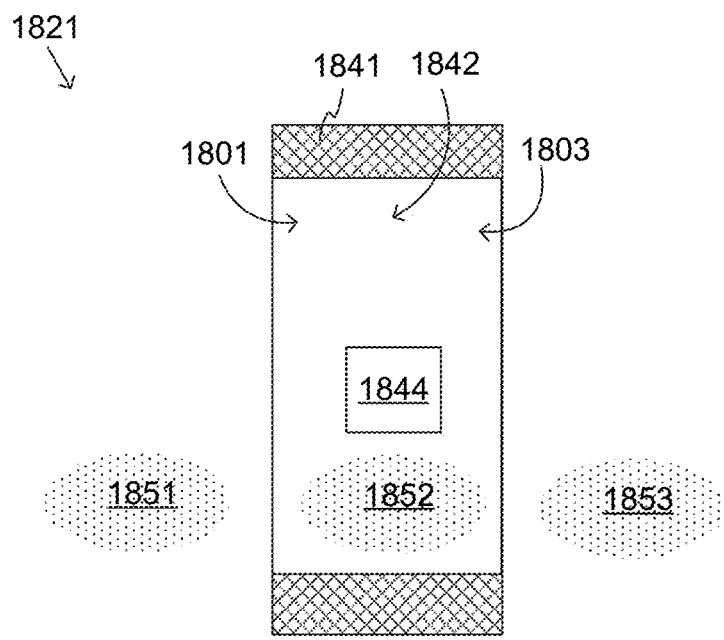
FIG. 18 is a side view of parts of a component of a sample sweat sensor according to embodiments.

FIG. 18 is a side view of parts 1821 of a component of a sample sensor for sensing sweating, made according to embodiments. Parts 1821 include a tube 1841, whose cross-section is shown. Tube 1841 has a cavity 1842, a person opening 1801 and a ventilation opening 1803 opposite person opening 1801. In other words, tube 1841 is open at both ends. Air 1852 in cavity 1842 communicates with air 1851, 1853 that is outside tube 1841, by the person opening 1801 and by ventilation opening 1803, respectively.

A hygrometer 1844 is coupled to tube 1841. Hygrometer 1844 can be configured to sense a humidity of air 1852 within cavity 1842. Hygrometer 1844 can be located wholly within tube 1841 as is preferred, or in part outside it.

Very briefly, tube 1841 is placed against a person, such as a patient, so that person opening 1801 is maintained against the person. Any sweat from the person thus increases the humidity of air 1852 within cavity 1842, which in turn can be sensed by hygrometer 1844. In a steady state, air 1852 vents to outside air 1853 at a regular rate, either directly or through clothes that are preferably not airtight. Hygrometer 1844 may be calibrated to thus sense and react to sudden and profuse amounts of sweating, while not reacting to gradual and small amounts of sweating. This may help in instances of detecting the onset of a heart attack, with fewer false alarms.

Tube 1841 may be made from a suitable material, such as hard plastic, metal, composites, etc. The side of the person opening 1801 may be smoothed for more comfortable contact with the person, and so on.

The dimensions of tube 1841 may be shaped in a number of ways, to facilitate what hygrometer 1844 will sense. Tube 1841 may have a length that is short enough to not rise too far from the skin of the patient and be thus relatively unobtrusive. In some embodiments, this length is between 1.25 cm and 5 cm, or approximately 0.5" to 2". Person opening 1801 may be wide enough to sample enough of the skin area, such as from 1 cm$^2$ to 10 cm$^2$, so as not to depend on a small area of the skin. Wider such areas permit the height to be less, while cavity 1842 still has enough volume to average enough air for a humidity measurement that is substantially stable over time that has no sudden events of sweating. In addition, tube 1841 is shown as having a certain length, and a substantially constant cross section throughout the length. This, however is not necessary, and the tube may expand or contract along its length.

While this is the preferred embodiment, other embodiments are also possible. For example, in this instance the only openings of cavity 1842 are person opening 1801 and ventilation opening 1803. Other openings are possible, in various ways, such as round holes, slits, etc.

Figure 19:
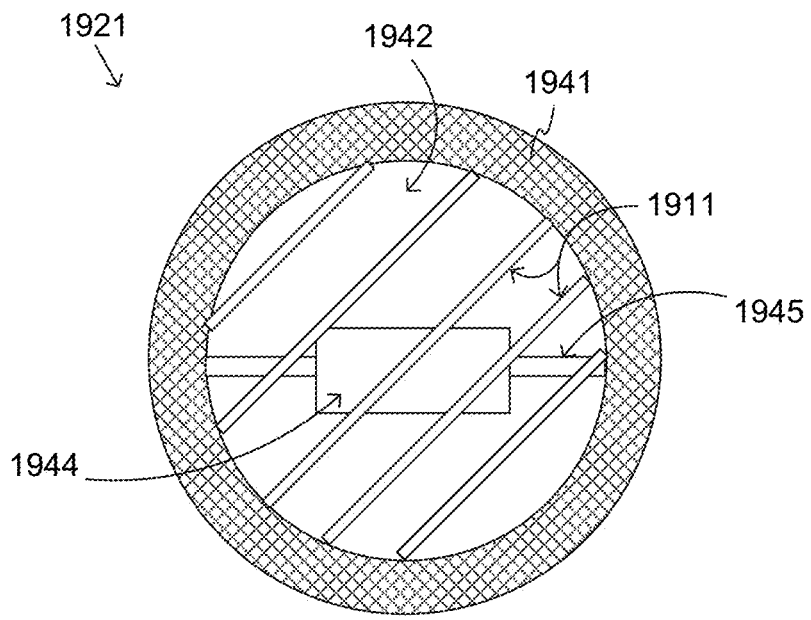
FIG. 19 is a top view of a sample sweat sensor that uses embodiments of the parts of FIG. 18.

FIG. 19 is a top view of a sample sensor 1921 that uses embodiments of parts 1821. A tube 1941 has a substantially circular cross section, although that is not required. The cross section may be oval-shaped, with the long axis maintained horizontal across the chest of the patient. Tube 1941 has a cavity 1942.

Hygrometer 1944 is located wholly within tube 1941. Sensor 1921 further includes a support member 1942 across tube 1941 and within cavity 1942. Hygrometer 1944 is attached to support member 1942, and thus is located closer to the center of cavity 1942.

In some embodiments, a grid is further provided to protect the hygrometer from accidental contact, or tampering. In some of these embodiments, the grid is provided between the hygrometer and the ventilation opening. In the example of FIG. 19, grid 1911 is provided at the ventilation opening. When a grid is provided, the hygrometer may even be coupled to the grid, and not need support member 1942.

Grid 1911 may be made from a suitable material. In embodiments, grid 1911 is constructed as one piece with tube 1941, for example such as hard plastic from a single mold.

Figure 20A:
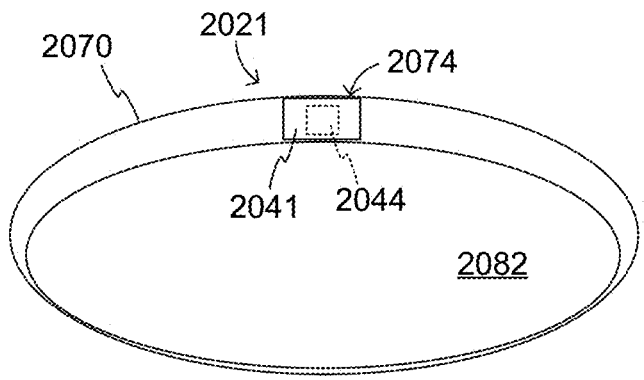
FIG. 20A is a diagram of a sample sweat sensor, made according to embodiments that use the parts of FIG. 18.

FIG. 20A is a section view of a sweat sensor 2021 made according to embodiments, which is being worn by a patient 2082. In particular, a section of the torso of patient 2082 is seen from the top. Patient 2082 is wearing a support structure 2070. In this particular example, support structure 2070 is a vest 2070, which may optionally have an opening at location 2074. The opening may be a complete opening, or a portion of vest 2070 that has multiple openings or perforations for ventilation to the outside. In other embodiments, support structure 2070 could be a band that surrounds the torso, etc.

Sweat sensor 2021 is supported on patient 2082 by support structure 2070. Sweat sensor 2021 has a tube 2041 that is held against the torso by support structure 2070. A hygrometer 2044 is within tube 2041, similarly to what was described above.

Figure 20B:
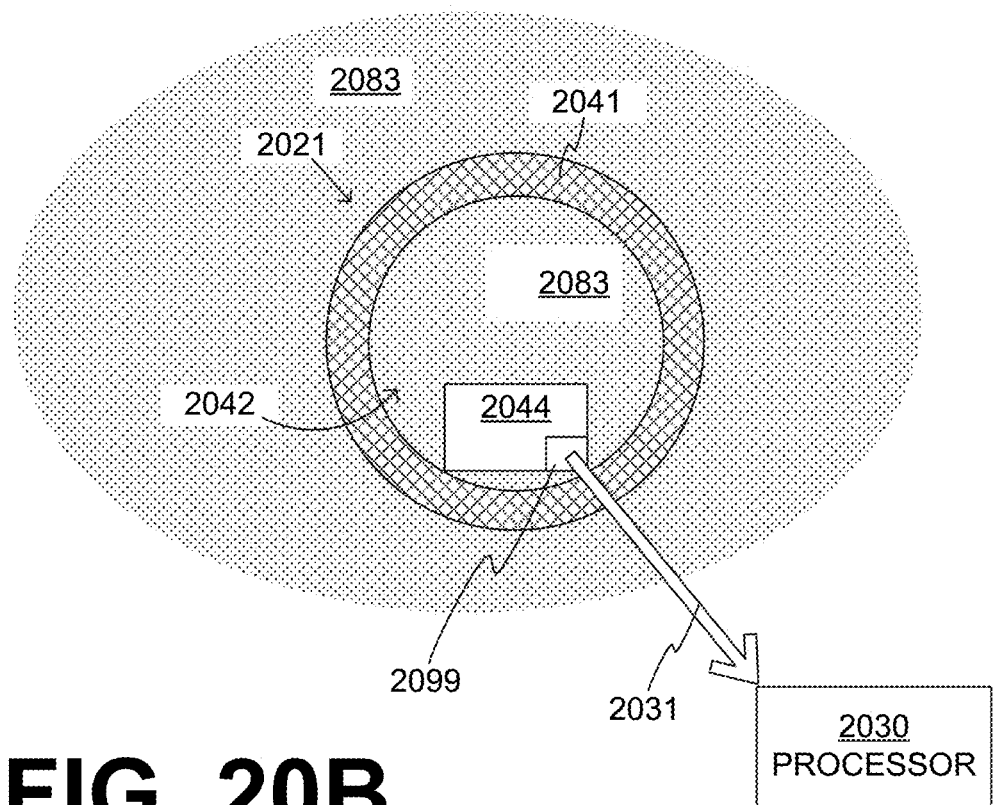
FIG. 20B is a diagram of a detail of a sample embodiment of the sweat sensor of FIG. 20A.

FIG. 20B is a top view of a detail of a sample embodiment of sweat sensor 2021 of FIG. 20A. Patient 2082 has a skin 2083, which is parallel to the plane of the drawing. Skin 2083 is indicated as a shaded area, but without a line surrounding it.

Tube 2041 is round, and has an open-ended cavity 2042. Skin 2083 of the patient is visible both outside tube 2041, and through tube 2041.

Tube 2041 thus rises vertically from skin 2083 without widening or constricting, similar to a short chimney or exhaust pipe for skin 2083 to vent to the outside. Cavity 2042 is completed at the bottom by skin 2083, and by the top by any portion of support structure 2070, and any other garments of patient 2082 worn outside support structure 2070. Hygrometer 2044 is attached to the inside of wall 2041.

Hygrometers 1844, 1944, 2044 may be made in a number of ways. In some such ways, the basic design of an ordinary environmental hygrometer is used as a starting point. An ordinary environmental hygrometer is used for measuring humidity of spaces such as rooms, basements, wine cellars etc., and many embodiments are available commercially, some online, costing only a few dollars. Given the cost of this and other parts, this patient sweat sensor may be made economically.

For embodiments, the basic design of an ordinary environmental hygrometer does not need a visual display for reading the sensed humidity. Rather, an output component 2099 of hygrometer 2044 is considered. Output component 2099 can be configured to communicate a notification signal to a processor 2030, according to an arrow 2031. Processor 2030 may be any of the processors described elsewhere in this document. Output component 2099 can include a port for a wired signal, or an antenna for a wireless notification, and so on. If wired, one or two additional wires from processor 2030 or another component, may provide power to hygrometer 2044, so that it does not need its own battery, etc. Any wires can be threaded to a support structure that is worn, so that they have less chance of being caught and pulled inadvertently by something else.

In embodiments, a wearable medical (WM) system includes electrodes for pacing a patient with heart failure. The pacing may result in halting and even reversing the heart failure. The WM system may even be an external Wearable Cardioverter Defibrillator (WCD) system.

In such embodiments, the WM system is configured to give shocks to a patient suffering from at least certain types of Congestive Heart Failure (CHF). With regular treatment, the CHF condition is expected to be reversed within a few months. This saves the patient from having surgery to implant an electrical device that would administer the shocks internally.

Congestive Heart Failure (CHF) is not an event, such as a heart attack, but a disease. Heart failure is the leading cause of hospitalization in people older than 65. In developed countries, the mean age of patients with heart failure is 75 years old. In developing countries, two to three percent of the population have heart failure, but in those 70 to 80 years old, it occurs in 20-30 percent of the population.

More than 20 million people have heart failure worldwide. In the United States, heart failure affects 5.8 million people, and each year 550,000 new cases are diagnosed.

Congestive heart failure (CHF), often referred to as Heart failure (HF), occurs when the heart is unable to pump sufficiently to maintain blood flow to meet the body's needs. Signs and symptoms commonly include shortness of breath, excessive tiredness, and leg swelling. The shortness of breath is usually worse with exercise, while lying down, and may wake the person at night. A limited ability to exercise is also a common feature. Chest pain, including angina, does not typically occur due to heart failure.

There are different types of CHF. In some instances, CHF is treated presently by surgery, where a device is implanted, and provides Cardiac contractility modulation (CCM) signals, for CCM therapy. The CCM signals are administered to the heart at appropriate moments in the rhythm of the patient. This helps; in some instances, there can be improvement of the symptoms, quality of life, and exercise tolerance. This can be advantageously combined with cardiac resynchronization therapy. CHF may even reversed, as genes expression can be restored.

There are problems with the surgery for implantation, however, not to mention the expense. There can be bleeding at the site where the system was implanted, and pneumonia. And surgeries are tough on patients who are older.

In some embodiments, Cardiac Contractility Modulation (CCM) therapy is provided externally, by using a suitably adapted Wearable Cardioverter Defibrillator system. One such adaptation would be for electrical pulses that have energies closer to pacing than defibrillation. In fact, some embodiments of a WCD system are already configured to deliver pacing pulses.

As such, Cardiac contractility modulation (CCM) can be delivered according to embodiments to patients with moderate to severe left ventricular systolic heart failure (NYHA class II-IV), which enhances both the strength of ventricular contraction and the heart's pumping capacity. Accordingly, patients may be treated with heart failure with normal QRS complex duration (120 msec or less).

Figure 21:
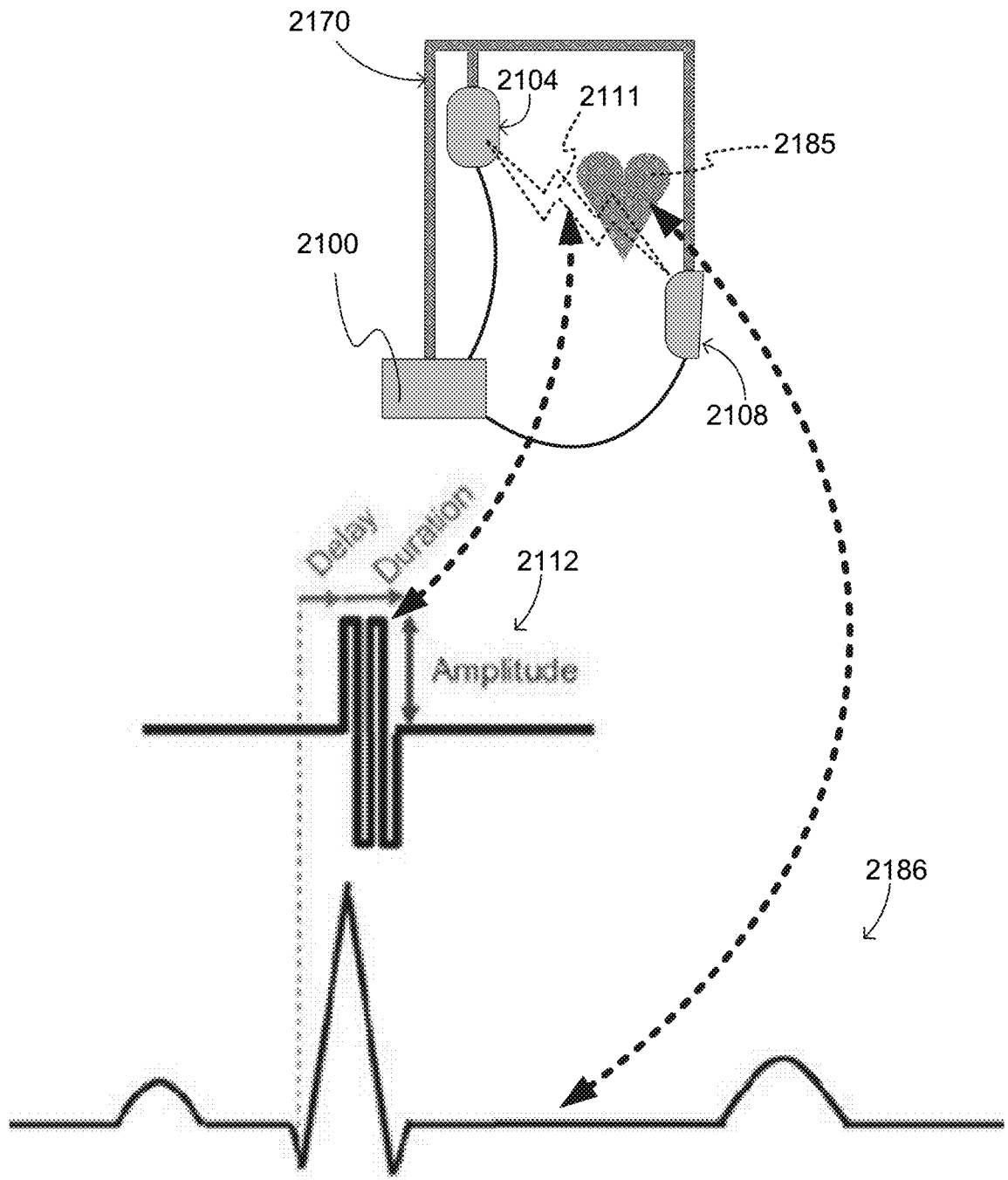
FIG. 21 is a diagram of a sample external Wearable Medical (WM) system delivering electrical pulses to correct Heart Failure, made according to embodiments.

FIG. 21 is a diagram of a sample external Wearable Medical (WM) system delivering electrical pulses to correct Heart Failure, made according to embodiments. the patient wears a support structure 2170, which can be as described for support structure 170. An electronics module 2100 can provide appropriate voltages to electrodes 2104, 2108. The electrodes cause a pulse 2111 to be delivered to through the patient's heart 2185.

Heart 2185 may have an ECG signal 2186, as the patient is not suffering SCA. Pulse 2111 can have a waveform 2112. Such cardiac contractility modulation (CCM) signals are biphasic pulses. The diagram further shows a possible synchronization of waveform 2112 with ECG signal 2186. In this diagram, the synchronization is to deliver the pulse after a defined delay from detection of local electrical activation. Other synchronizations may be possible. The synchronization portion of this drawing is from an article where electrical pulses are provided internally, and is titled: New devices in heart failure: an European Heart Rhythm Association report, Developed by the European Heart Rhythm Association; By: Karl-Heinz Kuck, Pierre Bordachar, Martin Borggrefe, Giuseppe Boriani, Haran Burri, Francisco Leyva, Patrick Schauerte, Dominic Theuns, Bernard Thibault, Europace (2014) 16, 109-128 doi:10.1093/europace/eut311, which is incorporated herein by reference.

In embodiments, CCM signals can be delivered ~30 ms after detection of the QRS complex onset, and consist of two biphasic +7 V pulses spanning a total duration of ~20 ms. These signals do not elicit a new action potential or contraction, as is the case with extra- or post-extrasystolic contractions. Moreover, they do not affect the sequence of electrical or mechanical activation, nor do they recruit additional contractile elements. On this basis, CCM signals are referred to as 'non-excitatory'.

Figure 22:
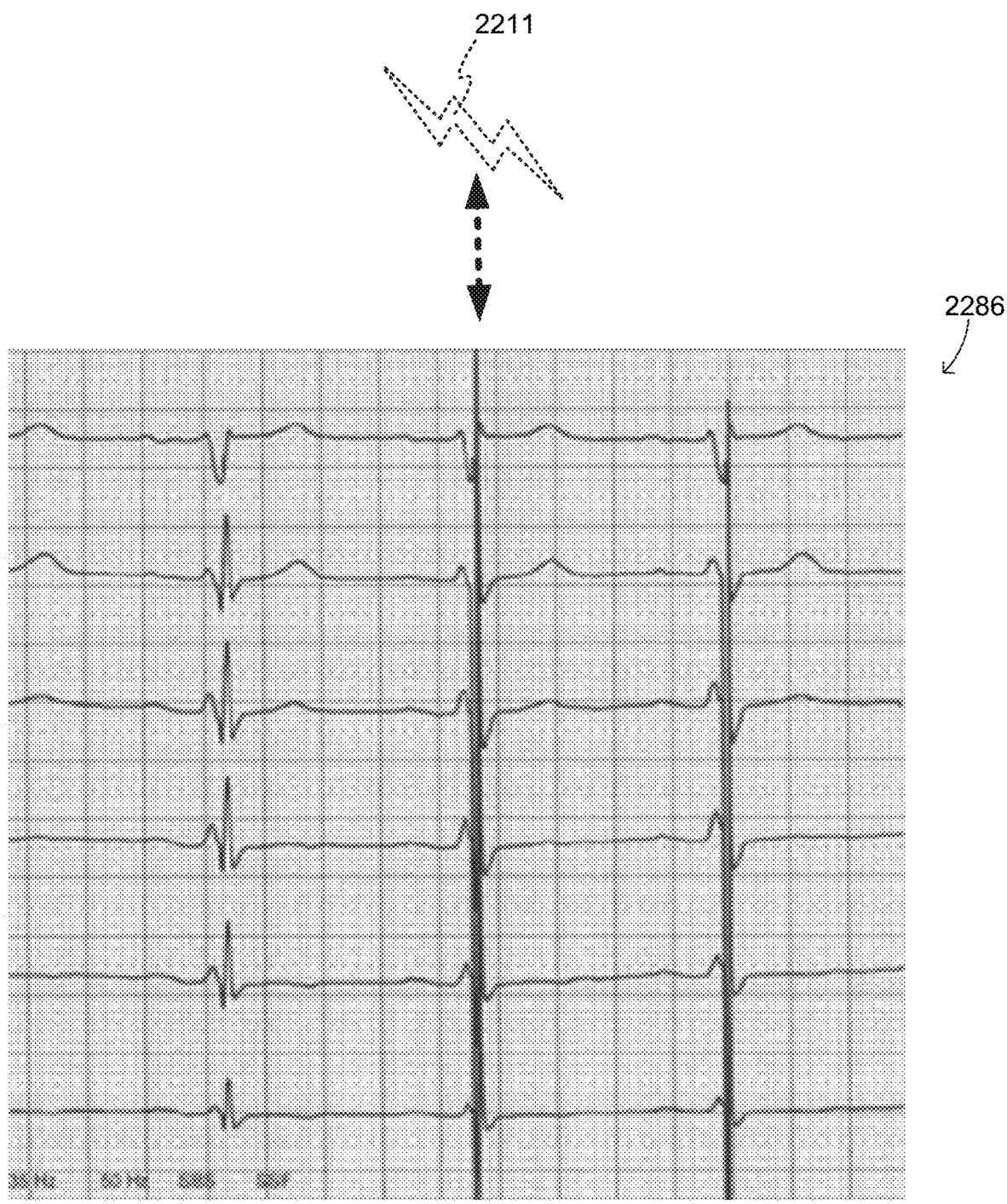
FIG. 22 is a time diagram of a sample waveforms according to embodiments of FIG. 21.

FIG. 22 is a time diagram of a sample waveforms according to embodiments of FIG. 21. ECG signal 2286 may be Body surface electrocardiogram (leads V1-V6). ECG electrodes may be supported on support structure 2170, which are more akin to a 12-lead configuration.

An electric pulse 2211 can be as pulse 2111, and is applied relative to ECG signal 2286 when shown by the arrow. ECG signal 2186 shows one beat prior to initiating CCM signals and the first two beats of CCM signal application. The stimulation artefact in Beats 2 and 3 reflect CCM signals.

Of course, for embodiments, the WM system is adapted so that it detects the QRS signal for knowing when to deliver the CCM pulses, as shown in FIG. 21. In addition, since the pulses are applied externally, they are of larger energy, so they have the same effect on the heart. Their size can be computed by determining the ratio of energies for external defibrillation to defibrillation by an ICD, and adjusted by that ratio so as to provide what is shown in FIG. 21.

Treatment can take place at regular times, e.g. during the evenings. A challenge with this approach is that the patient is conscious, and the pain may be too much. Transvenous pacing is painless, but transthoracic pacing is generally not tolerated by conscious patients. A conscious patient would immediately press the divert button or remove the vest to stop the pain.

One solution is to apply analgesia. A pain-reducing drug can be delivered to the patient, perhaps even by the WM system. One way of delivering a pain-reducing drug is to include the drug in the therapy electrode electrolyte. This electrolyte is released onto the patient's skin prior to a shock, either pacing or defibrillation. If the electrolyte included an analgesic such as lidocaine it may deaden the skin and surrounding tissue enough to reduce the pain. Skin patches with a 5% solution of lidocaine is sometimes used for treatment of pain associated with neuralgia. A similar concentration should also be effective for reducing pacing pain.

Another solution, possibly in combination with analgesia, is sedation. While an analgesic reduces the pain sensation locally, a sedative has a more systemic effect that reduces the general sensation of pain. It may make the patient drowsy or groggy to the point where they don't care about the pain. A drug such as propofol may be included in the electrolyte at an appropriate dosage that it can provide a light sedation through the skin. Propofol is a fast acting drug that, unlike many sedatives, has a minimal effect on blood pressure. Propofol patches have been shown to produce a sedative effect in rats, and the administration of electrical pacing pulses may enhance absorption of the drug.

To facilitate absorption of the drugs it is possible that the device might execute a different sequence of preparatory steps for pacing than defibrillation. For defibrillation, no drug absorption is necessary, so a shock can be delivered as soon as possible after electrolyte release. For pacing, an additional delay may be included after electrolyte release to allow time for the drug to penetrate the skin.

Drug absorption may also be increased by the introduction of a small electrical current. A current flow at a level that is imperceptible to the patient can enhance drub absorption. Prior to applying pacing pulses to the patient the WMS may release the electrolyte and apply a low-level current for a short period of time (possibly 1 minute) prior to initiation of pacing. This should reduce the pain of the first pacing pulses. The pacing pulses themselves will continue to facilitate drug absorption as the pulses are delivered, but it is also possible that a small drug-infusion current could be continued simultaneously with pacing.

It should be appreciated that the drugs listed here are just examples of drugs that might be used. The idea is to have one drug that acts as a local pain reliever and a second drug that provides a systemic effect.

Drug concentrations could be tailored to the patient's needs. A patient with a larger body mass may require a larger dosage to achieve the desired benefit. By prescribing a higher concentration solution for larger patients it may be possible to adjust the dosage for individual patients.

A WMS is particularly well suited for transcutaneous drug delivery because it already had a mechanism for releasing electrolyte to the patient's skin. The electrolyte typically serves as a coupling agent for defibrillation or pacing energy, but it can also serve to administer medication that may be beneficial.

While this disclosure is describes the benefits of applying and analgesic and/or a sedative to patients being paced, it is possible that there are other drugs that may benefit WCD patients. For example, epinephrine is often given to cardiac arrest patients to increase their blood pressure post-cardiac arrest. It could be beneficial for that purpose in WCD patients, or it could be found to be beneficial for bradycardia patients to accelerate their heart rate. In that case, it is possible that the WCD might release the electrolyte solely for the purpose of applying medication instead of external pacing. In fact, epinephrine may be more beneficial for treatment of bradycardia than external pacing so transdermal drug delivery may be preferred over external pacing.

In the methods described above, each operation can be performed as an affirmative act or operation of doing, or causing to happen, what is written that can take place. Such doing or causing to happen can be by the whole system or device, or just one or more components of it. It will be recognized that the methods and the operations may be implemented in a number of ways, including using systems, devices and implementations described above. In addition, the order of operations is not constrained to what is shown, and different orders may be possible according to different embodiments. Examples of such alternate orderings may include overlapping, interleaved, interrupted, reordered, incremental, preparatory, supplemental, simultaneous, reverse, or other variant orderings, unless context dictates otherwise. Moreover, in certain embodiments, new operations may be added, or individual operations may be modified or deleted. The added operations can be, for example, from what is mentioned while primarily describing a different system, apparatus, device or method.

A person skilled in the art will be able to practice the present invention in view of this description, which is to be taken as a whole. Details have been included to provide a thorough understanding. In other instances, well-known aspects have not been described, in order to not obscure unnecessarily this description.

Some technologies or techniques described in this document may be known. Even then, however, it does not necessarily follow that it is known to apply such technologies or techniques as described in this document, or for the purposes described in this document.

This description includes one or more examples, but this fact does not limit how the invention may be practiced. Indeed, examples, instances, versions or embodiments of the invention may be practiced according to what is described, or yet differently, and also in conjunction with other present or future technologies. Other such embodiments include combinations and sub-combinations of features described herein, including for example, embodiments that are equivalent to the following: providing or applying a feature in a different order than in a described embodiment; extracting an individual feature from one embodiment and inserting such feature into another embodiment; removing one or more features from an embodiment; or both removing a feature from an embodiment and adding a feature extracted from another embodiment, while providing the features incorporated in such combinations and sub-combinations.

In general, the present disclosure reflects preferred embodiments of the invention. The attentive reader will note, however, that some aspects of the disclosed embodiments extend beyond the scope of the claims. To the respect that the disclosed embodiments indeed extend beyond the scope of the claims, the disclosed embodiments are to be considered supplementary background information and do not constitute definitions of the claimed invention.

In this document, the phrases "constructed to", "adapted to" and/or "configured to" denote one or more actual states of construction, adaptation and/or configuration that is fundamentally tied to physical characteristics of the element or feature preceding these phrases and, as such, reach well beyond merely describing an intended use. Any such elements or features can be implemented in a number of ways, as will be apparent to a person skilled in the art after reviewing the present disclosure, beyond any examples shown in this document.

Incorporation by reference: References and citations to other documents, such as patents, patent applications, patent publications, journals, books, papers, web contents, have been made throughout this disclosure. All such documents are hereby incorporated herein by reference in their entirety for all purposes.

Reference numerals: In this description a single reference numeral may be used consistently to denote a single item, aspect, component, or process. Moreover, a further effort may have been made in the preparation of this description to use similar though not identical reference numerals to denote other versions or embodiments of an item, aspect, component or process that are identical or at least similar or related. Where made, such a further effort was not required, but was nevertheless made gratuitously so as to accelerate comprehension by the reader. Even where made in this document, such a further effort might not have been made completely consistently for all of the versions or embodiments that are made possible by this description. Accordingly, the description controls in defining an item, aspect, component or process, rather than its reference numeral. Any similarity in reference numerals may be used to infer a similarity in the text, but not to confuse aspects where the text or other context indicates otherwise.

The claims of this document define certain combinations and subcombinations of elements, features and acts or operations, which are regarded as novel and non-obvious. The claims also include elements, features and acts or operations that are equivalent to what is explicitly mentioned. Additional claims for other such combinations and subcombinations may be presented in this or a related document. These claims are intended to encompass within their scope all changes and modifications that are within the true spirit and scope of the subject matter described herein. The terms used herein, including in the claims, are generally intended as "open" terms. For example, the term "including" should be interpreted as "including but not limited to," the term "having" should be interpreted as "having at least," etc. If a specific number is ascribed to a claim recitation, this number is a minimum but not a maximum unless stated otherwise. For example, where a claim recites "a" component or "an" item, it means that the claim can have one or more of this component or this item.

In construing the claims of this document, the inventor(s) invoke 35 U.S.C. § 112(f) only when the words "means for" or "steps for" are expressly used in the claims. Accordingly, if these words are not used in a claim, then that claim is not intended to be construed by the inventor(s) in accordance with 35 U.S.C. § 112(f).

What is claimed is:

1. A wearable medical (WM) system for an ambulatory patient, comprising:
   electrocardiogram (ECG) electrodes;
   a support structure configured to be worn by the ambulatory patient to maintain the ECG electrodes on a body of the ambulatory patient, the ECG electrodes configured to sense an ECG signal of the ambulatory patient;
   an output device;
   a memory configured to store a reference template, the reference template made from one or more early portions of the ECG signal of the ambulatory patient that are sensed during a first time duration; and
   a processor configured to:
      input a test portion of the ECG signal of the ambulatory patient that is sensed during a second time duration, the second time duration starting at least 10 min after the first time duration ends,
      compare a value of a test aspect of the inputted test portion with a value of a reference aspect of the reference template stored in the memory to determine a difference, and
      cause the output device to output an alert responsive to the difference exceeding an alert threshold;
   wherein a default template is stored in the memory, and the difference is determined by comparing the value of the test aspect of the inputted test portion with a value of a reference aspect of the default template instead of with the value of a reference aspect of the reference template before the reference template is made or completed.

2. The WM system of claim 1, further comprising:
a defibrillation electrode, the support structure further configured to maintain the defibrillation electrode on the body of the ambulatory patient; and
an energy storage module configured to store an electrical charge and to discharge the stored electrical charge via the defibrillation electrode through the ambulatory patient so as to deliver a shock to the ambulatory patient.

3. The WM system of claim 1, in which
the default template was constructed from prior data of prior patients.

4. The WM system of claim 1, in which
the default template was constructed from prior data of prior patients who match the ambulatory patient in at least one demographic parameter of a set that includes gender, age, height and weight.

5. The WM system of claim 1, in which
the processor is further configured to
select an amplitude waveform of a certain one of the one or more early portions of the ECG signal, and
store the selected amplitude waveform in the memory as the reference template.

6. The WM system of claim 1, in which
the processor is further configured to
generate a composite amplitude waveform from early amplitude waveforms of respective ones of the early portions of the ECG signal, and
store the composite amplitude waveform in the memory as the reference template.

7. The WM system of claim 6, in which
the processor is further configured to identify similarity statistics of early amplitude waveforms of respective ones of the early portions of the ECG signal, and
in which the composite amplitude waveform is generated from those of the early amplitude waveforms whose similarity statistics exceed a threshold.

8. The WM system of claim 6, in which
the processor is further configured to align the early amplitude waveforms, before generating the composite amplitude waveform from them.

9. The WM system of claim 8, in which
the processor is further configured to filter the early amplitude waveforms prior to aligning them.

10. The WM system of claim 6, in which
the processor is further configured to
determine whether a normal condition was met when a certain one of the early portions of the ECG signal was sensed, and
use the early amplitude waveform of the certain early portion to generate the composite amplitude waveform responsive to determining that the certain early portion was sensed when a normal condition was met.

11. The WM system of claim 10, in which
the normal condition includes that a heart rate of the patient is less than a heart rate threshold.

12. The WM system of claim 10, further comprising:
a monitoring device configured to monitor at least one physiological parameter of the ambulatory patient that is not the ECG signal of the ambulatory patient; and
the normal condition is met responsive to a value of the monitored parameter being less than a normal threshold.

13. The WM system of claim 12, in which
the monitoring device includes a motion detector.

14. The WM system of claim 12, in which
the physiological parameter is one chosen from the ambulatory patient's heart rate, blood perfusion, blood flow, blood pressure, blood oxygen level, pulsatile change in light transmission or reflection properties of perfused tissue, heart sounds, breathing sounds, pulse and motion.

15. The WM system of claim 1, in which
a certain one of the ECG electrodes is coupled to the support structure, the coupling such that, while the support structure is worn by the ambulatory patient, the certain ECG electrode is at one of an unbiased state in which the certain ECG electrode is moveable with respect to the patient's body responsive to the patient's moving such that the certain ECG electrode occasionally loses contact with the patient's body, and a biased state in which the certain ECG electrode is mechanically biased towards the patient's body against the support structure to be less moveable with respect to the patient's body than when in the unbiased state, and
further comprising:
a biasing mechanism configured to cause the certain ECG electrode to transition from the unbiased state to the biased state, and
in which the certain ECG electrode is configured to sense the ECG signal when the certain ECG electrode has transitioned to the biased state.

16. The WM system of claim 15, in which
the biasing mechanism is configured to cause the certain ECG electrode to transition from the unbiased state to the biased state responsive to determining that a monitoring condition is met.

17. The WM system of claim 1, in which
the processor is further configured to determine whether a monitoring condition is met, and
the test portion is input responsive to determining that the monitoring condition is met.

18. The WM system of claim 17, in which
the processor further includes a clock configured to keep a time, and
the monitoring condition is met responsive to the time reaching a checking moment.

19. The WM system of claim 17, in which
the monitoring condition includes that a heart rate of the patient is above a heart rate threshold.

20. The WM system of claim 17, further comprising:
a monitoring device configured to monitor at least one physiological parameter of the ambulatory patient that is not the ECG signal of the ambulatory patient; and
the monitoring condition is met responsive to a value of the monitored parameter reaching a monitoring threshold.

21. The WM system of claim 20, in which
the monitoring device includes a motion detector.

22. The WM system of claim 20, in which
the physiological parameter is one chosen from the ambulatory patient's heart rate, blood perfusion, blood flow, blood pressure, blood oxygen level, pulsatile change in light transmission or reflection properties of perfused tissue, heart sounds, breathing sounds, pulse and motion.

23. The WM system of claim 20, further comprising:
a user interface (UI) having an input device that is configured to be actuated by the ambulatory patient, and in which the monitoring condition is met responsive to the ambulatory patient actuating the input device.

24. The WM system of claim 1, in which
the test aspect includes an aggregated waveform of the test portion of the ECG signal.

25. The WM system of claim 1, in which
the test aspect includes a QRS interval of a QRS complex of the inputted test portion of the ECG signal.

26. The WM system of claim 1, in which
the test aspect includes an ST segment after a QRS complex of the inputted test portion of the ECG signal.

27. The WM system of claim 1, in which
the test aspect includes an ST interval of a QRS complex of the inputted test portion of the ECG signal.

28. The WM system of claim 1, in which
the test aspect includes a T-wave after a QRS complex of the inputted test portion of the ECG signal.

29. The WM system of claim 1, in which
the difference is determined as a computed waveform similarity coefficient, and
the alert is output responsive to the computed waveform similarity coefficient being below a similarity threshold.

30. The WM system of claim 29, in which
the waveform similarity coefficient is computed according to equation 1377 in FIG. 13 of this document.

31. The WM system of claim 1, in which
the processor is further configured to store in the memory an event responsive to the difference exceeding the alert threshold.

32. The WM system of claim 1, in which
the WM system includes a user interface (UI),
the output device belongs to the UI, and
the alert is output by the output device emitting a human-perceptible indication.

33. The WM system of claim 1, in which
the WM system includes a communication module that is the output device, and
the alert is output by the communication module transmitting a notification to another device.

34. The WM system of claim 1, in which
the memory further stores a table that lists a plurality of possible ailments of the ambulatory patient,
the processor is further configured to look up, from the stored table, a certain one of the possible ailments responsive to a morphology of the test portion of the ECG signal, and
the alert includes an indication for the certain ailment.

35. A non-transitory computer-readable storage medium storing one or more programs which, when executed by at least one processor of a wearable medical (WM) system, the WM system further including electrocardiogram (ECG) electrodes, a support structure configured to be worn by an ambulatory patient to maintain the ECG electrodes on a body of the ambulatory patient, the ECG electrodes configured to sense an ECG signal of the ambulatory patient, an output device, and a memory configured to store a reference template, the reference template made from one or more early portions of the ECG signal of the ambulatory patient that are sensed during a first time duration, these one or more programs result in operations comprising:

storing a reference template in the memory, the reference template made from one or more early portions of the ECG signal of the ambulatory patient that are sensed during a first time duration;
inputting a test portion of the ECG signal of the ambulatory patient that is sensed during a second time duration, the second time duration starting at least 10 min after the first time duration ends;
comparing a value of a test aspect of the inputted test portion with a value of a reference aspect of the reference template stored in the memory to determine a difference; and
causing the output device to output an alert responsive to the difference exceeding an alert threshold;
wherein a default template is stored in the memory, and
the difference is determined by comparing the value of the test aspect of the inputted test portion with a value of a reference aspect of the default template instead of with the value of a reference aspect of the reference template before the reference template is made or completed.

36. A method for a wearable medical (WM) system, the WM system including a processor, a memory, an output device, electrocardiogram (ECG) electrodes, a support structure configured to be worn by an ambulatory patient to maintain the ECG electrodes on a body of the ambulatory patient, the ECG electrodes configured to sense an ECG signal of the ambulatory patient, the method comprising:
storing a reference template in the memory, the reference template made from one or more early portions of the ECG signal of the ambulatory patient that are sensed during a first time duration;
inputting a test portion of the ECG signal of the ambulatory patient that is sensed during a second time duration, the second time duration starting at least 10 min after the first time duration ends;
comparing a value of a test aspect of the inputted test portion with a value of a reference aspect of the reference template stored in the memory to determine a difference; and
outputting, by the output device, an alert responsive to the difference exceeding an alert threshold;
wherein a default template is stored in the memory, and
the difference is determined by comparing the value of the test aspect of the inputted test portion with a value of a reference aspect of the default template instead of with the value of a reference aspect of the reference template before the reference template is made or completed.

37. The method of claim 36, wherein
the test aspect includes an ST segment after a QRS complex of the inputted test portion of the ECG signal; and
the reference aspect includes an ST segment after a QRS complex of the stored reference template.

38. The method of claim 36, wherein
the test aspect includes an ST interval after a QRS complex of the inputted test portion of the ECG signal; and
the reference aspect includes an ST interval after a QRS complex of the stored reference template.

* * * * *